US006914723B2

(12) United States Patent
Yun et al.

(10) Patent No.: US 6,914,723 B2
(45) Date of Patent: Jul. 5, 2005

(54) REFLECTIVE LITHOGRAPHY MASK INSPECTION TOOL BASED ON ACHROMATIC FRESNEL OPTICS

(75) Inventors: Wenbing Yun, Walnut Creek, CA (US); Yuxin Wang, Arlington Heights, IL (US)

(73) Assignee: Xradia, Inc., Concord, CA (US)

( * ) Notice: Subject to any disclaimer, the term of this patent is extended or adjusted under 35 U.S.C. 154(b) by 78 days.

(21) Appl. No.: 10/427,723

(22) Filed: Apr. 29, 2003

(65) Prior Publication Data

US 2004/0057107 A1 Mar. 25, 2004

Related U.S. Application Data

(63) Continuation-in-part of application No. 10/289,151, filed on Nov. 5, 2002, which is a continuation-in-part of application No. 10/134,026, filed on Apr. 25, 2002, application No. 10/427,723, which is a continuation-in-part of application No. 10/134,026.
(60) Provisional application No. 60/337,752, filed on Nov. 9, 2001, provisional application No. 60/338,362, filed on Nov. 9, 2001, provisional application No. 60/337,277, filed on May 1, 2002, and provisional application No. 60/376,499, filed on Apr. 29, 2002.

(51) Int. Cl.$^7$ .............................................. G02B 27/44
(52) U.S. Cl. ....................... 359/565; 359/569; 359/576; 359/350; 359/355; 359/361

(58) Field of Search ................................. 359/565, 558, 359/569, 576, 571, 350, 355, 361, 365, 368, 393

(56) References Cited

U.S. PATENT DOCUMENTS

| 5,161,057 A | | 11/1992 | Johnson |
| 5,161,059 A | | 11/1992 | Swanson et al. |
| 5,349,471 A | | 9/1994 | Morris et al. |
| 5,453,880 A | | 9/1995 | Vanderwerf |
| 5,559,338 A | | 9/1996 | Elliott et al. |
| 5,926,318 A | | 7/1999 | Hebert |
| 5,946,281 A | * | 8/1999 | Ito et al. ................. 369/112.07 |
| RE36,352 E | * | 10/1999 | Swanson et al. ............. 359/565 |
| 6,285,737 B1 | | 9/2001 | Sweatt et al. |
| 6,483,638 B1 | | 11/2002 | Shafer et al. |
| 2002/0005938 A1 | | 1/2002 | Omura |

FOREIGN PATENT DOCUMENTS

| EP | 1 006 400 A2 | 6/2000 |
| EP | 1 006 400 A3 | 5/2003 |

* cited by examiner

*Primary Examiner*—Fayez G. Assaf
(74) *Attorney, Agent, or Firm*—John P. O'Banion

(57) ABSTRACT

A mask blank inspection tool includes an AFO having a diffractive lens and a refractive lens formed on a common substrate. The diffractive lens is a Fresnel zone plate and the refractive lens is a refractive Fresnel lens. The AFO is used to image light from a defect particle on a multilayer mask blank or the surface of the multilayer mask blank to a detector.

31 Claims, 18 Drawing Sheets

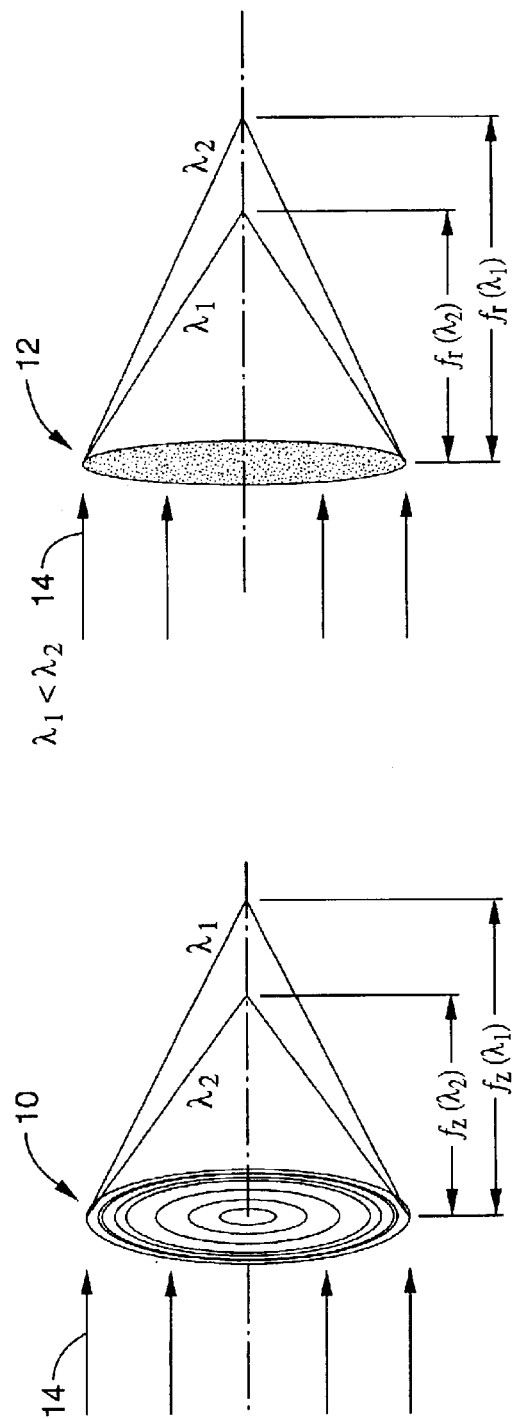
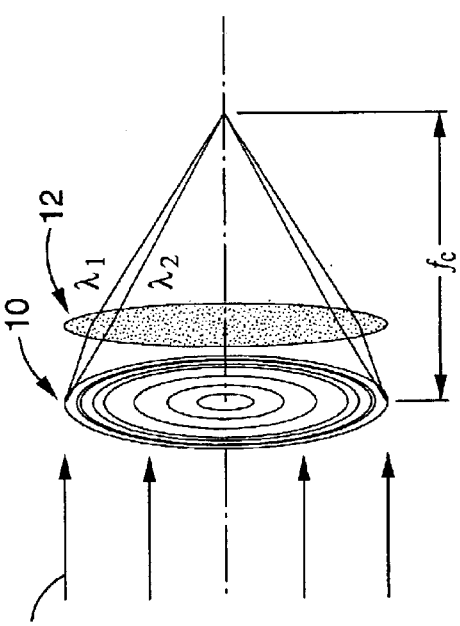
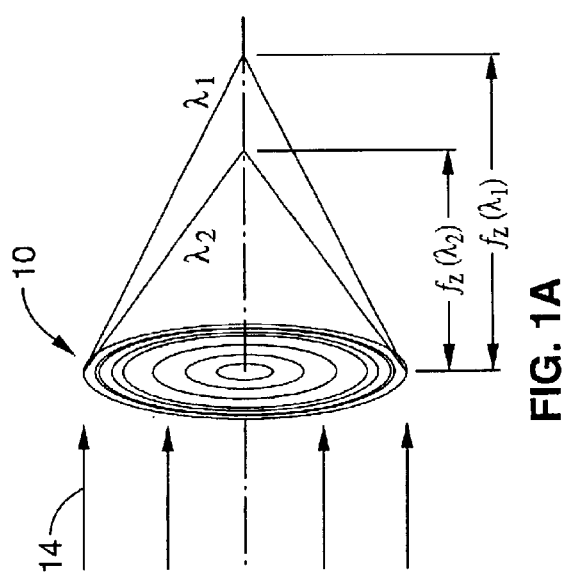

REFLECTIVE LITHOGRAPHY MASK INSPECTION TOOL BASED ON ACHROMATIC FRESNEL OPTICS

CROSS-REFERENCE TO RELATED APPLICATIONS

This application is a continuation-in-part of copending application Ser. No. 10/289,151 filed on Nov. 5, 2002, which is a continuation-in-part of copending U.S. application Ser. No. 10/134,026 filed on Apr. 25, 2002, incorporated herein by reference, which claims priority from U.S. provisional application Ser. No. 60/337,752 filed on Nov. 9, 2001, incorporated herein by reference, and from U.S. provisional application Ser. No. 60/338,362 filed on Nov. 9, 2001, incorporated herein by reference.

This application is also continuation-in-part of copending application Ser. No. 10/134,026 filed on Apr. 25, 2002, incorporated herein by reference, which claims priority from U.S. provisional application Ser. No. 60/337,752 filed on Nov. 9, 2001, incorporated herein by reference, and from U.S. provisional application Ser. No. 60/338,362 filed on Nov. 9, 2001, incorporated herein by reference.

This application also claims priority to U.S. provisional application Ser. No. 60/377,277 filed on May 1, 2002 and to U.S. provisional application Ser. No. 60/376,499 filed on Apr. 29, 2002.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention pertains generally to lithography, and more specifically to lithography methods using short wavelength electromagnetic radiation.

2. Description of Related Art

Lithography has been the key enabling technology for the steady performance improvement in semiconductor integrated circuit (IC) devices over the last thirty years. By reducing the feature size, the density of components as well as the speed and functionality of microchips have doubled every two to three years. The current generation of lithography methods employ visible or ultraviolet light and refractive lens objectives to image the mask pattern onto a pattern-forming resist layer on a wafer and subsequently develop the latent image to complete a pattern transfer process. Since the printable feature size is limited by the wavelength of the light, ever decreasing wavelengths are being used for lithography applications. Further reduction in wavelength using current refractive lens-based lithography methods can be extremely difficult and is limited by a lack of suitable materials for making the imaging lenses.

This difficulty was recognized more than ten (10) years ago and alternative lithography methods (collectively known as the next-generation lithography methods) are currently being developed. The next-generation lithography (NGL) methods employ either charged particle beams, e.g., electron and ion, or electromagnetic radiations having wavelengths substantially shorter than one-hundred and fifty-seven nanometers (157 nm)—the shortest wavelength to be used in the current generation lithography tools. At various times, next-generation lithography methods have included proximity X-ray lithography, ion projection lithography, extreme ultraviolet lithography (EUVL), and electron beam projection lithography (EPL). Presently, EUVL and EPL are considered the most promising candidates.

The EUVL method employs extreme ultraviolet radiation having a wavelength of approximately thirteen nanometers (13 nm). A EUVL lithography camera typically consists of 4 to 6 aspherical multilayer mirrors arranged at near-normal incidence, which require a demanding mult gradation in multilayer period across the optic) on large diameter aspherical optical mirror surfaces with figure control at almost the atomic level. The camera is not axially symmetric but has a ring-shaped printing field. To produce an illumination field matching that of the printing field of the camera, a condenser consisting of a large number of multilayer mirrors is required. For example, the Engineering Test Stand (ETS) developed by the EUVL LLC and the virtual national laboratory has ~20 multilayer mirrors in the condenser and has 4 multilayer mirrors in the camera. Radiation arriving at the photoresist experiences nine reflections from its origin at the source. The number of multilayer mirrors and thus the number of reflections in the camera may increase by two in EUVL cameras designed to achieve resolution better than 50 nm. Because of the large number of multilayer mirrors must be used, only a small percentage of the EUV source power is delivered to the wafer, while a large amount flare is added to the exposure. The large number of multilayer mirrors also imposes stringent requirement on the precise matching of the multilayer spacings, alignment, mechanical and vibrational stability. Consequently the costs of initial tool, replacement, and maintenance are extremely high.

Camera designs based on optics developed for x-ray microscopy have also been proposed. Transmission objectives developed for x-ray focusing and imaging applications include zone plates and compound refractive lenses. A compound refractive lens consists of many spherical or parabolic shaped lenses aligned along the optical axis. A large number of individual lenses are needed to obtain a short effective focal length because the focal length is inversely proportional to the number of lenses, which typically have a focal length of tens to hundreds of meters. Therefore, compound refractive lenses are not likely to be useful as objectives in the next generation lithography methods because they do not have the required numerical aperture with an acceptable system throughput.

Zone plates consist of concentric rings with alternative materials. The positions of the rings are determined by a simple equation and the ring width decreases with increasing radius. They are currently the highest resolution transmissive optic, demonstrating a resolution of better than 25 nm in the 2–5 nm spectral region. The focal length of a zone plate lens is inversely proportional to wavelength and therefore the zone plate is highly chromatic. This chromaticity precludes its application in lithographic imaging cameras since an illumination beam with an extremely narrow spectral bandwidth would be required to limit chromatic aberrations should a printing field of sufficient size be required. This would consequently severely limit the energy from the source that can be used for exposing the photoresist.

BRIEF SUMMARY OF THE INVENTION

The present invention discloses an inspection and metrology method for multilayer mask blanks and patterned multilayer masks using imaging systems based on achromatic Fresnel optic(s) (AFO) that operate(s) at or near the wavelength at which the multilayer are designed to operate. The multilayer mask blanks and the patterned multilayer masks are typically, but not limited to, used in lithography for printing integrated circuits (IC) using 10–15 nm wavelength extreme ultraviolet radiation.

The disclosed method offers several major advantages. First, the imaging property of the AFO allows both the imaging of the structure of a patterned multilayer mask and the detection and imaging of defects on a multilayer mask blank. Since the operating wavelength of the AFO operates at or near the designed operating wavelength of the multilayers, the disclosed imaging system closely resembles the operation of the printing process. In such an actinic systems, only the relevant defects on a multilayer mask blank or only the printable structures on a patterned mask blank are imaged. It can be used in a bright field, dark field, or phase contrast imaging modes, similar to that a lens used in an optical microscope. Second, an AFO based imaging system can achieve a spatial resolution better than 25-nm, which has been demonstrated using zone plates at ~500 eV x-rays. Therefore structures on a patterned multilayer mask can be imaged with high resolution and high precision, allowing further classification of defects on a multilayer mask blank or a multilayer patterned mask to help identify the root cause of failures. Third, an AFO based imaging system can have a high throughput since the AFO can have a numerical aperture greater than 0.2. Fourth, an AFO based imaging system will efficiently utilize the energy from a broad-spectrum source since it can be designed with a bandwidth of up to 1.5%. Fifth, an AFO based imaging system can be constructed with a field of view of many millimeters, permitting the imaging of the structure of a patterned mask over a large area or the detection of defects over a large area of a mask blank.

The present invention also discloses four AFO-based imaging system designs for achieving specific functions and applications. In all four cases, the AFO is used to image the light from the defect particle or the multilayer surface to the detector. In the first two imaging system designs, the AFO is used in a dark field imaging mode, i.e., it does not intercept the beam illuminating the object, so that the image is created by photons that are scattered into the field of view by structures in the object. The first two imaging systems differ in their detectors and applications. The first imaging system design uses a single element detector to record the scattered photons as a function of the position of the object when it is scanned in a raster fashion. Its main application is for inspecting mask blanks for extreme ultraviolet lithography applications. The second imaging system uses an array detector with suitable spatial resolution. It is located at the imaging plane of the AFO while the test object is located at the object plane. Its main applications include performing metrology measurement of patterned multilayer masks or imaging and classifying defects on a multilayer mask blank. The third imaging system is essentially a microscope using the AFO as the objective operating in a bright field imaging mode. Its main applications include performing metrology measurement of a patterned multilayer masks or imaging and classifying defects on a multilayer mask blank. The fourth imaging system is a microscope using the AFO as the objective operating in a phase contrast imaging mode. Its main applications are similar to those of the dark field and the bright field imaging modes but may offer higher sensitivity with somewhat more complex optical train.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1A through FIG. 1C are schematic diagrams illustrating an AFO comprising a Fresnel zone plate and a refractive Fresnel lens according to the present invention.

DETAILED DESCRIPTION OF THE INVENTION

Figure 2:
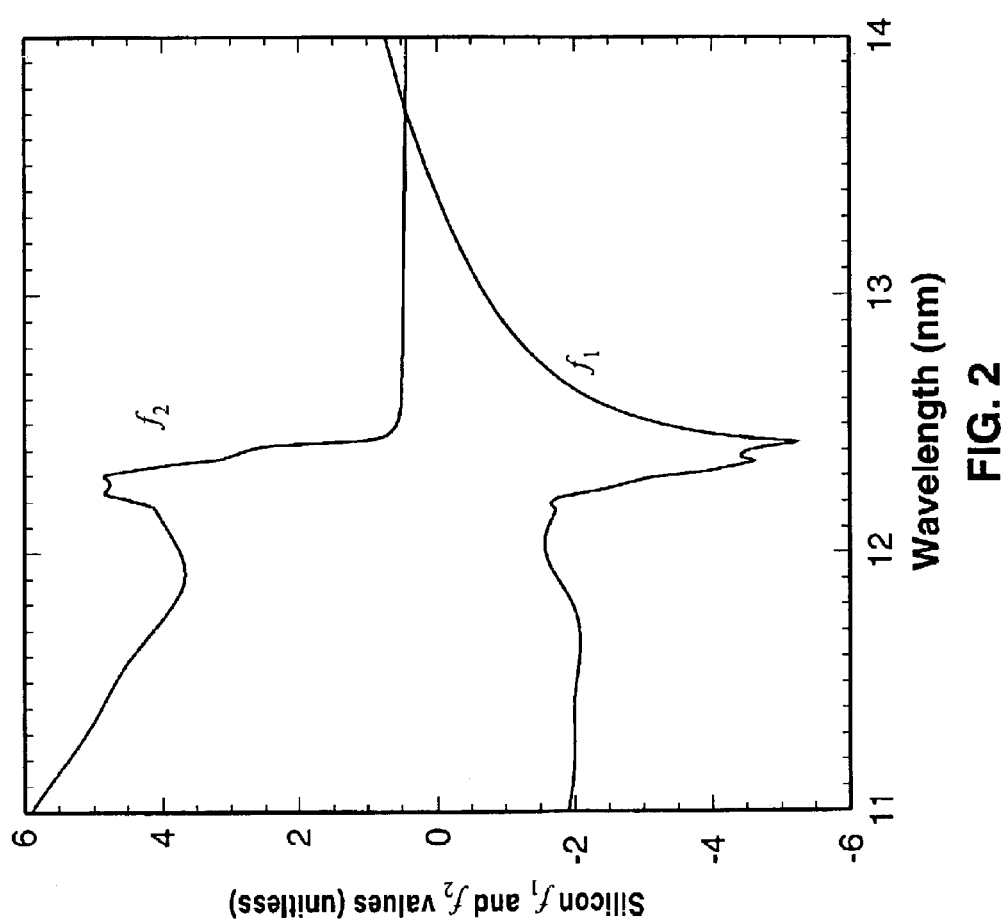
FIG. 2 is a graph of Silicon $f_1$ and $f_2$ values plotted versus radiation wavelength near the L-edge, illustrating the large change of $f_1$ as a function of wavelength near the absorption edge.

The preferred embodiments of reflective lithography mask inspection tools based on an achromatic Fresnel objective, or AFO lens, according to the present invention will now be described, as will the AFO lens upon which such tools are based.

The inventive AFO lens combines a diffractive Fresnel zone plate and a refractive Fresnel lens. It will be appreciated that a Fresnel zone plate is a diffractive imaging optic comprising a set of concentric rings with the ring (zone) width decreasing with radius and that several research groups have demonstrated imaging at sub-30 nm resolution in the 2–5 nm wavelength range, which is the highest resolution demonstrated for the entire spectrum of electromagnetic radiation. A Fresnel zone plate is characterized by its radius R, the width of the outermost zone $\Delta R$, and the number of zones N. The resolution of a zone plate according to the Rayleigh criteria is 1.22$\Delta R$ under appropriate illumination conditions. The imaging property of a zone plate is identical to that of a thin lens with a focal length.

$$f_z = \frac{2R\Delta R}{\lambda}.$$

The focal length is inversely proportional to the wavelength, and therefore chromatic. To obtain the intrinsic resolution 1.22 $\Delta R$ of a zone plate, image blurring due to chromatic aberration needs to be controlled. Up to now, the only method for controlling the chromatic aberration has been to use a beam with a sufficiently narrow spectral bandwidth. It is well established that the spectral bandwidth required is $$\frac{\Delta\lambda}{\lambda} = \frac{1}{N},$$

where N is the number of zones. This requirement effectively rules out zone plates as imaging optics in lithography because an extremely narrow spectral bandwidth is required for printing a large area with a high resolution. For example, printing a 10 mm$^2$ area with a 50 nm node size would require a spectral bandwidth less than 3×10$^{-5}$, which would mean that radiation from a source have to be monochromatized to an impractical level, leaving little power for exposing the resist.

The AFO of the present invention uses a refractive Fresnel lens to correct the zone plate's chromatic aberration and overcome its limitation for large-area and high-resolution imaging. This refractive Fresnel lens operates on similar principle of refraction as a conventional lens for visible light. The focal length of a refractive lens with a single refractive lens surface is given by $$f_r = -\frac{R_c}{\delta},$$

where $R_c$ is the lens radius of curvature, $1-\delta = 1-\alpha\lambda^2 f_1$ is the real part of the refractive index $n=1-\delta-i\beta$ of the lens material for EUV and shorter wavelength radiation, $\alpha$ is a constant dependent on the Fresnel lens material and lens thickness, and $f_1$ is the real part of atomic scattering factor. The focal length of the refractive Fresnel lens varies as $$f_r \propto \frac{R_c}{\lambda^2 f_1},$$

so that it is a chromatic lens and cannot be used alone as an imaging optic in lithography for the same limited-bandwidth reason that precludes use of a zone plate. The AFO takes advantage of the chromatic characteristics of both types of optics by combining a diffractive Fresnel zone plate and a refractive Fresnel lens such that the chromatic aberrations cancel. The resulting achromat can have a bandwidth of up to 5%.

Referring now to FIG. 1, the basic principles of the present invention can be seen. FIG. 1 shows a Fresnel zone plate 10 and a refractive lens 12. FIG. 1 shows that the zone plate 10 and lens are subjected to radiation 14 (e.g., EUV and x-ray) having two wavelengths, $\lambda_1$ and $\lambda_2$, where $\lambda_1 < \lambda_2$. As shown, the Fresnel zone plate focal length $f_z$ varies such that $f_z(\lambda_1) > f_z(\lambda_4)$. The present invention recognizes that it is possible to design a refractive Fresnel lens such that $f_r(\lambda_1) < f_r(\lambda_2)$, and to form a compound AFO comprising the Fresnel zone plate 10 with the refractive Fresnel lens 12, where the combined focal length $f_c$ is the same for both wavelengths and, in addition, wherein the focal length for all wavelengths between $\lambda_1$ and $\lambda_2$ fall within the depth of focus (DOF). For purposes of the discussion herein, we refer to the central wavelength $$\frac{\lambda_1 + \lambda_2}{2}$$

as the Designed Operating Wavelength (DOW). Accordingly, the present invention further recognizes that the optimal DOW of an AFO is near an absorption edge of an element making up the Fresnel lens because of the large wavelength dependence of $f_r$.

The principle behind the AFO of the present invention can be explained as follows. For a small wavelength increase, $\lambda \rightarrow \lambda + \Delta\lambda$, the focal length of a Fresnel zone plate is given by $$f_z(\lambda + \Delta\lambda) = \frac{f_z(\lambda)}{1 + \Delta\lambda/\lambda}.$$

For the refractive lens, both the wavelength variation $\lambda^2 \rightarrow \lambda^2 + 2\lambda\Delta\lambda + (\Delta\lambda)^2$ and the wavelength dependence in the effective number of electrons $f_1(\lambda)$ should be considered. Here, we use the lowest order term of the Taylor series expansion of $f_1(\lambda)$ as a good approximation; that is, $$f_1 \rightarrow f_1 + \frac{\Delta f_1}{\Delta\lambda}\Delta\lambda.$$

Keeping only first order variation terms, the focal length of the refractive lens can be expressed as $$f_r(\lambda + \Delta\lambda) = \frac{f_r(\lambda)}{1 + \frac{2\Delta\lambda}{\lambda} + \frac{\Delta f_1}{f_1}}. \qquad (2)$$

If two lenses are separated by a small distance s, their combined focal length is given by $$\frac{1}{f_c} = \frac{1}{f_z} + \frac{1}{f_r} - \frac{s}{f_z f_r}. \qquad (3)$$

In the limit $s \ll f_z f_r$, the focal length $f_c$ of the resulting compound optic made up of a Fresnel zone plate and a refractive lens is $$\frac{1}{f_c(\lambda + \Delta\lambda)} = \frac{1}{f_z(\lambda + \Delta\lambda)} + \frac{1}{f_r(\lambda + \Delta\lambda)} \qquad (4)$$

$$= \frac{1}{f_z(\lambda)}\left(1 + \frac{\Delta\lambda}{\lambda}\right) + \frac{1}{f_r(\lambda)}\left(1 + \frac{2\Delta\lambda}{\lambda} + \frac{\Delta f_1}{f_1}\right)$$

$$= \frac{1}{f_z(\lambda)} + \frac{1}{f_r(\lambda)} + \frac{\Delta\lambda}{\lambda}\left[\frac{1}{f_z(\lambda)} + \frac{1}{f_r(\lambda)}\left(2 + \frac{\lambda}{f_1}\frac{\Delta f_1}{\Delta\lambda}\right)\right]$$

From the foregoing, the key to the achromatic Fresnel objective can be seen; namely, the term in the last bracket [ ] is made zero so that there is no change in focal length over a wavelength range $\Delta\lambda$. This condition can be written as $$\frac{f_r(\lambda)}{f_z(\lambda)} = -\left(2 + \frac{\Delta f_1/f_1}{\Delta\lambda/\lambda}\right) = -(2+D), \qquad (5)$$

where $$D \equiv \frac{\Delta f_1/f_1}{\Delta\lambda/\lambda}$$

characterizes the dispersion, or the dependence of the refractive lens on the wavelength. It follows that the radius of curvature of the refractive lens can be determined as $$R_C = 2\alpha R\Delta R\lambda f_1(2+D). \qquad (6)$$

A similar analysis can be carried out if the separation between the AFO's two components is not negligible.

It will be appreciated that for the ease of fabrication of the refractive lens, it is advantageous to have a large radius of curvature, which requires a large dispersion. It is well known in anomalous dispersion theory that $f_1(\lambda)$ of a given material changes rapidly with wavelength near an absorption edge of a major element in the material. Therefore, for a given spectral range, it is preferred to make the refractive lens using a material containing an element having an absorption edge within the spectral range. In the case of a step-like rise in absorption as the wavelength is decreased (e.g., an EUV or x-ray absorption edge), $f_1(\lambda)$ has the shape of a "V" with the minimum of the dip occurring at wavelengths just above the wavelength of the absorption edge. The dependence of the refractive index near an absorption edge (also known as dispersion relation) is described by the Kramers-Krönig relation. FIG. 2 shows a plot of $f_1(\lambda)$ calculated using the Kramers-Krönig relation based on measured absorption data near the silicon L absorption edge. Within the "V" shaped spectral region, the value of D ranges from 50 to 100. In this spectral region, Equation (5) indicates that the focal length of the refractive lens is much larger than that of the Fresnel zone plate. Furthermore, Equation (6) can be approximated as:

$$R_C \approx 2\alpha R\Delta R\lambda f_1(2+D) \qquad (7)$$

$$= \alpha \times (2R\Delta R) \times \lambda^2 \times \frac{\Delta f_1}{\Delta\lambda}.$$

Here we see that the radius of curvature of the refractive lens depends on a constant $\alpha$, zone plate parameters R and $\Delta R$, designed operating wavelength $\lambda$, and the dispersion property $$\frac{\Delta f_1}{\Delta\lambda}$$

of the refractive lens material. It is generally preferable to use the long wavelength (lower in energy) part of the "V" spectral region because the absorption attenuation of the transmitted radiation is much lower than the corresponding short wavelength part. For material with absorption edges at much shorter wavelengths (less than 1 nm) where absorption is less of a concern, wavelengths above the absorption edge can be used. The required shape of the refractive lens is convex if the DOW is in longer than the wavelength corresponding to the minimum of $f_1(\lambda)$, and is concave if the DOW is shorter. Finally, since the focal length of the refractive lens 12 (FIG. 1) is much larger than the zone plate 10 (FIG. 1), the resolution and depth of field of the compound AFO are approximately equal to those of the Fresnel zone plate component.

Figure 3:
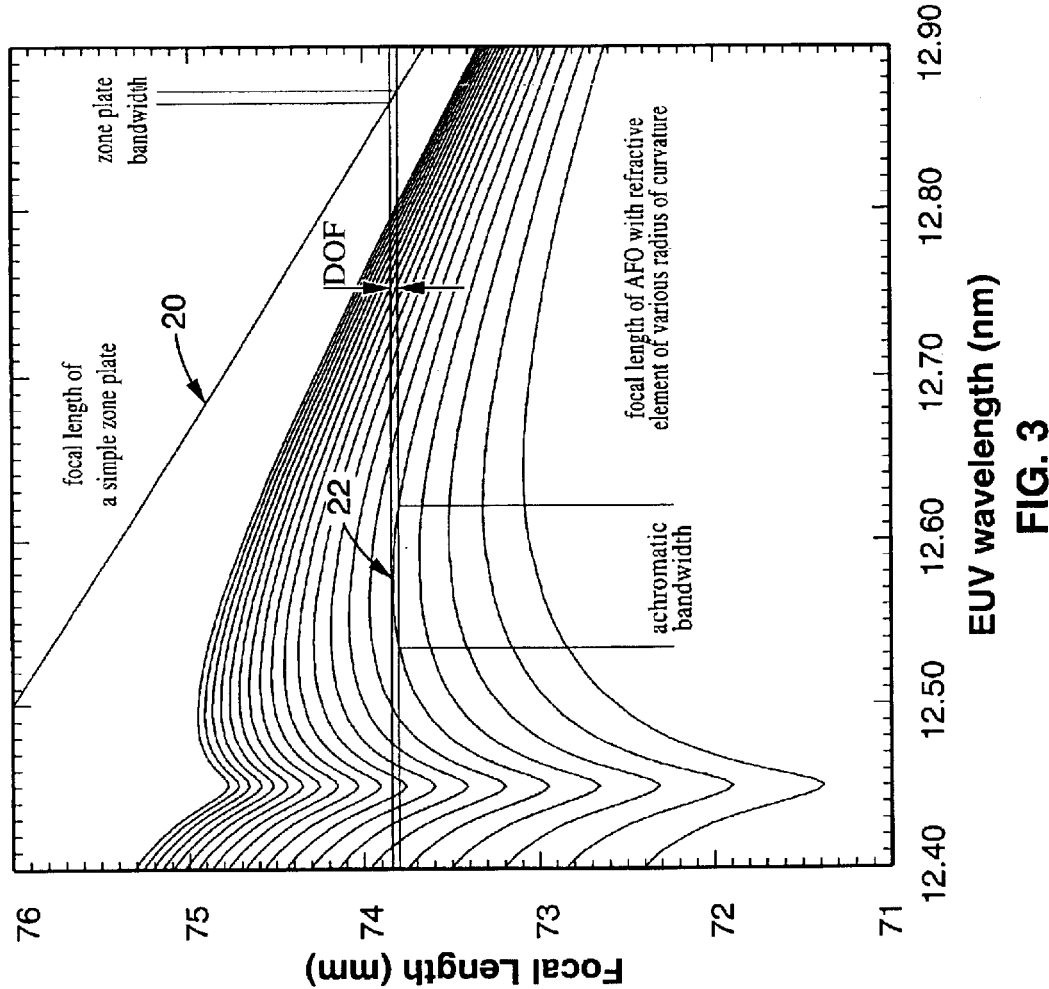
FIG. 3 is a graph comparing the focal length of a simple Fresnel zone plate and a compound AFO lens plotted as a function of radiation wavelength, illustrating that the dependence of the AFO's focal length on wavelength is substantially smaller than the Fresnel zone plate.

FIG. 3 shows the behavior of the combined focal length $f_c$, for an example of an AFO as a function of radiation wavelength compared to a simple zone plate. The wavelength dependence of $f_1$ is a key element to why the AFO of the present invention functions as described. Generally, $f_1$ varies slowly with wavelength and this rate of change is too small to be useful for chromatic correction. However, classical anomalous dispersion theory shows that $f_1$ varies quickly with wavelength near an absorption edge. When the wavelength of incident radiation decreases and approaches an absorption edge of an element making up the refractive Fresnel lens, the value of $f_1$ decreases rapidly and then increases rapidly (see FIG. 2). This occurs for elements of atomic number between 3–50 at wavelengths of approximately 1–20 nm. For silicon in the 12.6 to 13.5 nm wavelength region, the decrease in $f_1$ means that the focal length of a convex refractive Fresnel lens increases with wavelength, which is opposite to the wavelength dependence of the zone plate's focal length. Within the designed spectral bandwidth, the change in $f_r$ due to $f_1$ is significantly greater than that due to wavelength and is also much greater than the zone plate's focal length change. The relatively large dependence of $f_r$ on wavelength (large dispersion in optics terminology) not only permit its use for correcting the chromaticity of zone plate, but also makes its fabrication practical.

In FIG. 3, the upper straight line 20 shows that the focal length of the zone plate 10 is inversely proportional to the radiation wavelength. However, when combined with the refractive lens 12, as shown in FIG. 1, the straight line 20 can be bent so that within certain bandwidths, the combined focal length changes little (e.g., curved line 22), demonstrating that the AFO has much wider achromatic bandwidth than the Fresnel zone plate. It is to be understood that the two extreme or bandwidth-defining wavelengths can be selected such that $f_c$ for all wavelengths between them also falls within the depth of field. Moreover, because of the aforementioned difficulties associated with making refractive lenses, the Fresnel zone plate 10 is preferably the principal focusing element and the refractive lens 12 is preferably used to recombine the light of different wavelengths dispersed by the zone plate 10.

Figure 7:
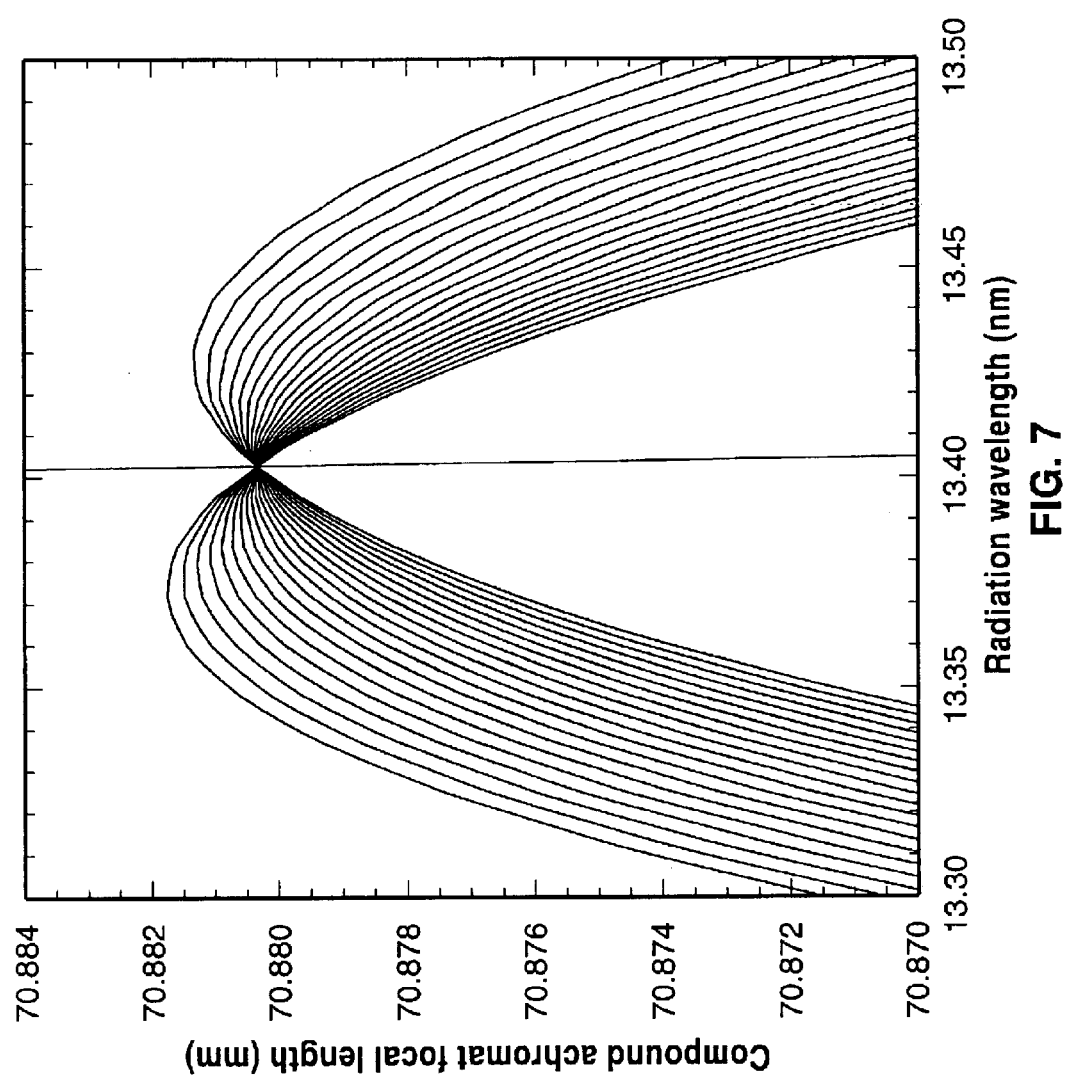
FIG. 7 is a graph of the combined focal length of an AFO according to the present invention having a silicon refractive lens plotted versus radiation wavelength.
Figure 8:
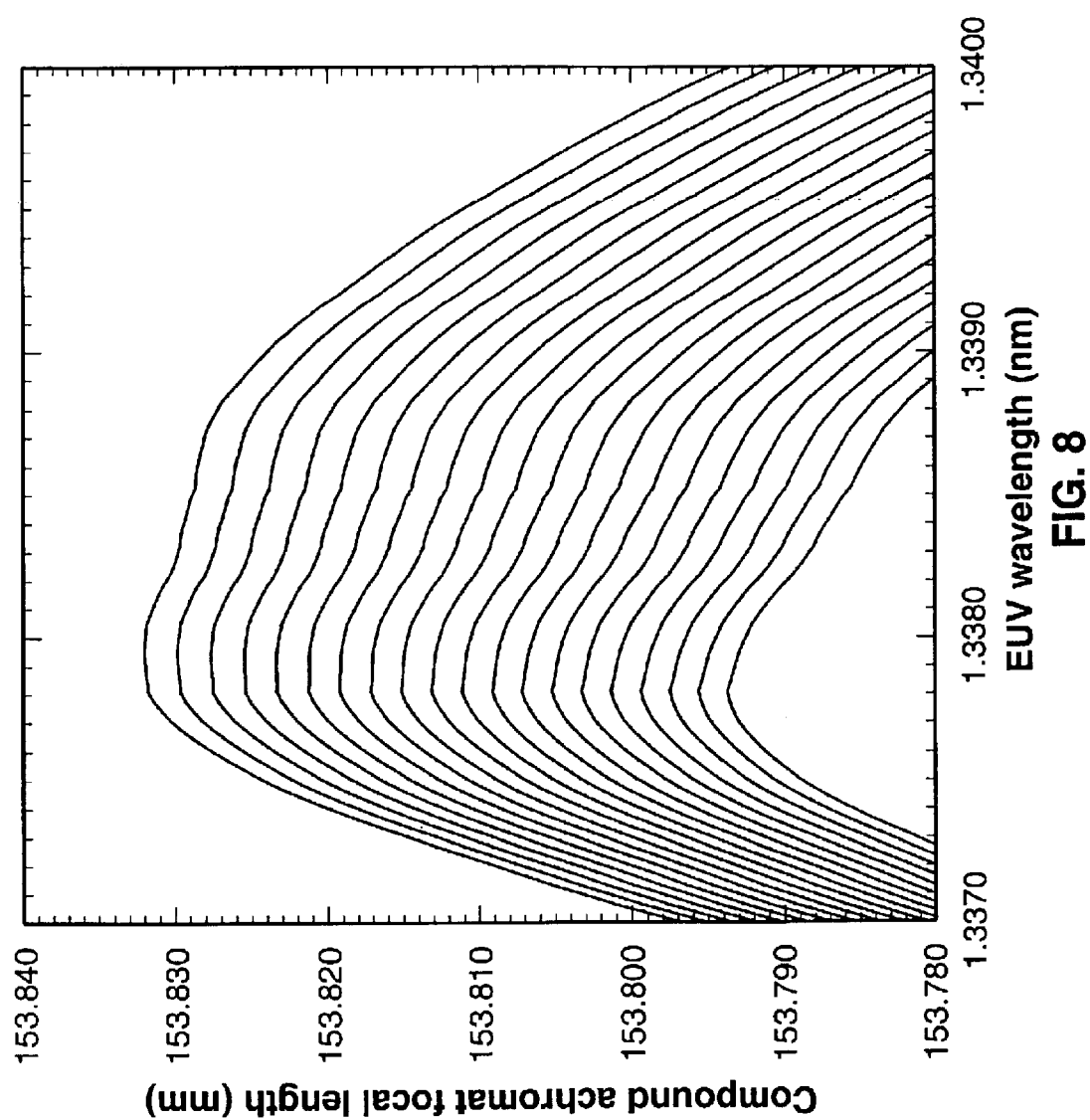
FIG. 8 is a graph of the combined focal length of an AFO according to the present invention having a copper refractive lens plotted versus radiation wavelength.

For example, an AFO with the desired optical parameters can be designed using suitable refractive Fresnel lens materials and appropriate geometry parameters. FIG. 7 shows the calculated focal length of an AFO as a function of wavelength for a silicon refractive lens. The focal length is contained in the depth of field of the lens, within ~1.2% spectral bandwidth near 13.4 nm. Note that the focal length of the zone plate is inversely proportional to wavelength, and the chromaticity correction is achieved by a refractive Fresnel lens made from Si which has an absorption edge near 13.4 nm. Similar parameters for an AFO with designed operation wavelength (DOW) near 1.3 nm using a copper refractive lens are shown in FIG. 8. This lens is clearly appropriate for x-ray lithography applications.

The degree of bending of radiation by the refractive lens depends on its radius of curvature. As shown in FIG. 3, the higher curves (closer to the simple zone plate) result from corrective refractive lenses with larger radius of curvature, or a weaker lens. As the radius is decreased (or as the refractive lens becomes stronger), the focal length of the compound lens deviates more from that of the simple zone plate and at the same time, the operating wavelength is shifted away from the absorption edge while the curve near the DOW becomes flatter, resulting in wider bandwidth. It is therefore recognized that the refractive lens has a strong influence on the DOW and the bandwidth. Consequently, its design must also take into account spectral characteristics of other components of the systems such as the source spectrum and condenser spectral response, etc. In practice, further considerations such as related fabrication technology and previous experience, etc. must also be included. For an example, much experience has been gained in EUV lithography programs for energies between ninety-five and one hundred electron volts (95 eV and 100 eV) and x-ray lithography programs for energies near one kilo electron volts (1 keV) energy. Sources, reflective optics, and monochromators are well developed for these energies. It is advantageous to leverage on these experiences and resources to develop the applications, discussed below, that uses the achromatic Fresnel lens of the present invention.

Another factor that must be considered when designing the AFO is the fabrication of the refractive lens in conjunction with the zone plate. Traditionally, zone plates have been fabricated on silicon substrates, much like microchips. Therefore, it is very convenient to use the same silicon substrate to fabricate the refractive lens thereon. Techniques for etching silicon with high accuracy have also been well developed. Material properties must also be considered. Silicon, chromium, and copper have all been used extensively for fabricating nanostructures and as such are the preferred materials for manufacturing the present invention.

A few non-limiting AFO design examples are listed in Table 1.

The maximum thickness $t_C$ of the refractive lens is:

$$t_C = R_C - \sqrt{R_C^2 - R^2} \approx \frac{R^2}{2R_C}. \quad (8)$$

Especially at EUV wavelengths, this thickness may be large enough to absorb an unacceptably large fraction of the incident intensity. One strategy for dealing with this issue is to replace the refractive lens with a refractive Fresnel lens so that the overall curvature can be maintained within a step-wise approximation while decreasing the refractive lens thickness to acceptable values.

Figure 5:
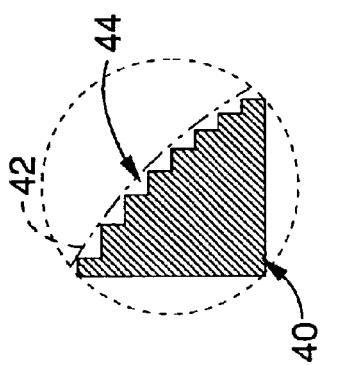
FIG. 5 is a detailed side view of a portion of the achromatic Fresnel optic of FIG. 4 showing a non-limiting example of a staircase profile that approximates the curved lens surface.
Figure 4:
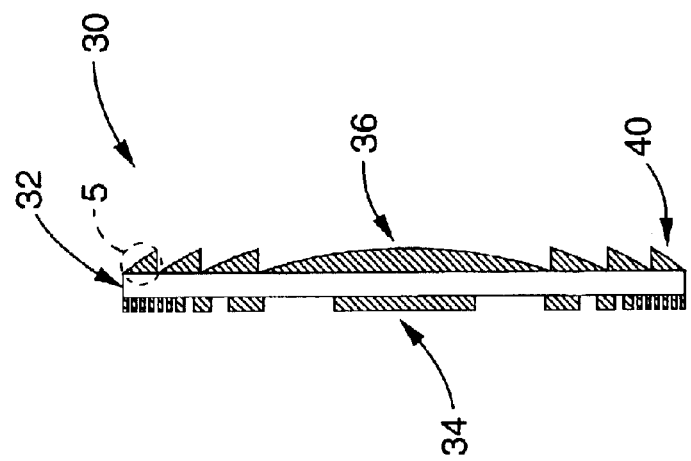
FIG. 4 is a side view of an achromatic Fresnel optic according to the present invention.

Referring now to FIG. 4 and FIG. 5, a preferred, non-limiting example of an AFO constructed from silicon is shown and generally designated 30. FIG. 4 shows that the AFO 30 includes a preferably silicon substrate 32 on which a silicon zone plate 34 and silicon refractive lens 36 are constructed. For example, a fine line width, binary grating structure 34 (i.e., a Fresnel zone plate) is fabricated on one side of a robust 0.25 micron thick silicon nitride window 32. On the other side of the same window, a series of three lithography steps can be used to pattern an eight-level Fresnel lens 36 that produces the desired refractive lens correction. It is important to realize that only one lithography step need be done at high resolution (the patterning of the Fresnel zone plate); the Fresnel lens, whose finest zones are of micron size, can be patterned at the resolution of existing optical steppers.

Figure 6:
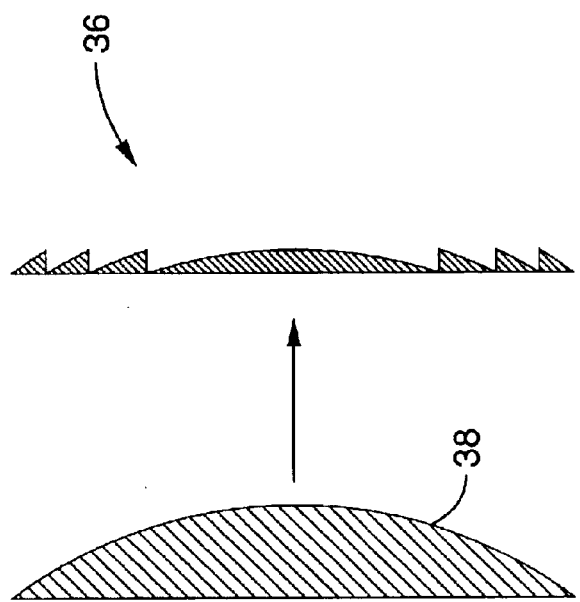
FIG. 6 is a side view of a simple refractive lens compared to a thinner refractive Fresnel lens of the type shown in FIG. 4.

It is to be understood that, since a simple refractive lens may be too thick for achieving acceptable transmission of short wavelength radiation, the preferred refractive lens 36 is a refractive Fresnel lens for improving the throughput of the AFO. For example referring to the leftmost portion of FIG. 6, a simple refractive lens 38 listed in the first row of Table 1 having a central thickness of 0.42 mm is too thick to use with EUV light having an 1/e absorption of 0.55 μm. As shown in the rightmost portion of FIG. 6, the solution is to produce a thinner refractive Fresnel lens 36, preferably on the same substrate as the zone plate 34 as shown in FIG. 4.

If the maximum thickness of the refractive Fresnel lens 36 is 1.25 μm, corresponding to 2 π phase at the DOW, approximately 20% average transmission can be achieved. Such a Fresnel lens has about three-hundred and forty bands 40. Much like a diffractive zone plate, the width of the bands are coarse near the center of the lens and finer near the edge. In the preferred design, the outermost band is about 7.4 μm, which can be produced with photo-induced chemical etching techniques. In practice, a smooth difficult to produce accurately, but the curvature 42 can be approximated by making a plurality of steps 44 in each band as shown in FIG. 5. With current nano-fabrication technology, zone plates with efficiency of 50% have been demonstrated. This yields a combined efficiency of about 10% for the achromatic lens. It is to be understood that the above construction method is preferred because large separation values, s, have the tendency of decreasing the bandwidth. Also, fabricating both elements on the same substrate makes it easier to align them and maintain that alignment. It is, however, also possible to construct both lens elements on separate substrates and align them later. This separate construction method may simplify the fabrication procedures at large-scale production beyond the prototype demonstration.

Note that the 2 π phase shift depth is only exactly true for the DOW. At other wavelengths within the bandwidth, a small wavefront error of 0.01 λ to 0.1 λ will occur. However, the degradation to the performance of the lens from this error may be negligible for most applications.

To further improve the throughput of the compound optic, the maximum thickness of the Fresnel lens can be made thinner to arbitrary thickness while the phase error introduced can be canceled by adjusting the zone positions of the Fresnel zone plate. As a non-limiting example, we may choose the make the maximum thickness of the Fresnel lens to be 0.625 μm, corresponding to π phase shift. Then the rays from neighboring bands will arrive at the focal point out of phase and therefore fail to focus. We can shift the position of the zones (rings) of the zone plate that lie within alternate bands by one zone (half the zone/space period). Consequently, an additional $\pi$ phase shift is produced by the zone plate, canceling the $\pi$ generated by the refractive lens. This example would have about combined efficiency of about 25%, more than doubling the previous one with maximum thickness corresponding to 2 $\pi$ phase shift. It is noted that this method is practical since the zone plate is most often patterned by an electron beam writer typically with a much higher positioning accuracy than the zone width.

For electromagnetic radiation of wavelength loner than about 1 nm, the $f_1$ value of many elements crosses zero during its pre-edge decline (see FIG. 2). If the DOW is designed to be the zero-crossing point, the refractive Fresnel lens can be of arbitrary thickness, while requiring no additional compensation from the zone plate. In this case, the Fresnel lens acts as an absorber and a wavelength (counter) disperser: for radiation exactly at the DOW, no phase shift is produced. While radiation at other wavelengths within the bandwidth will be dispersed according to design to converge at the focal point, no net phase shift is produced. This is the preferred regime to construct an achromat according to the methods discussed above.

The size of the zone plate and imaging field are likely to be limited by the primary aberrations. When imaging finite conjugates with object distance p and image distance q for off-axis angle of $\theta$, the Seidel wavefront (primary) aberrations are:

$$\text{spherical aberration: } \frac{3r^4(q-f)}{8f^2q^2} \quad (9)$$

$$\text{coma: } \leq \frac{\theta r^3}{2}\left(\frac{1}{q^2} - \frac{1}{p^2}\right) \quad (10)$$

$$\text{astigmatism: } -\frac{r^2\theta^2}{2f} \quad (11)$$

$$\text{field curvature: } -\frac{r^2\theta^2}{4f} \quad (12)$$

The distortion term is always zero, i.e. a Fresnel zone plate always produces distortion-free images. To obtain diffraction-limited images, these terms should be kept under $\lambda/4$.

As a non-limiting example, we first look at the maximum zone plate size and image field size attainable for an AFO without any monochromatic aberration correction for 4:1 demagnifying imaging. At DOW of 1.33 nm, the AFOs in Table 1 have outer most zone width of between 41 nm and 95 nm, hence the numerical apertures are quite small, ranging from 0.032 to 0.014. Imaging fields between 2 mm and 15 mm can be obtained. When used with EUV radiation at 12.5 nm wavelength, the numerical apertures are increased nearly ten fold. The primary aberrations become problematic when the zone plate consists of more than a few hundred zones. For an example, for a zone plate with 95 nm outer zone width, diffraction limited images can be obtained if the zone plate has a diameter of less than 0.5 mm and an imaging field of 0.15 mm. This can be increased significantly if aberration corrections are applied. A well-known technique used in designing refractive lenses for visible light regime is to adjust the bending factor defined as $$B = \frac{R_2 + R_1}{R_2 - R_1} \quad (13)$$

where $R_1$ and $R_2$ are the lens radii of curvature. A zone plate can be interpreted as a hologram produced by a reference wave originating from distance $R_{Ref}$ and a point object from distance $R_{Obj}$. The bending factor for a zone plate can then be similarly defined as $$B = \frac{R_{Ref} - R_{Obj}}{R_{Ref} - R_{Obj}}. \quad (14)$$

It has been shown that by adjusting the value of B, all primary aberrations of a zone plate can be simultaneously minimized. For an example, by computing zones for specific finite conjugate imaging, spherical aberration can be eliminated completely at the designed conjugates. (It will, however, appear at other conjugates.) In accordance with the present invention, we exploit this property to correct the aberrations of an AFO: namely, the astigmatism and field curvature can be reduced by increasing the size of the AFO while maintaining the same of the field of view. Coma can be reduced or eliminated by placing a field aperture near or at the natural position. The distortion term is zero. That is, a zone plate, and therefore an AFO, produces distortion-free images.

Referring to FIG. 7, the focal length of the AFO 30 listed in the fourth row of Table 1 is shown as a function of energy for various refractive lens radius of curvature. From the graph, it can be observed that the if the radius of curvature is 6 mm, a bandwidth of 1.2 eV or 1.3% can be achieved. As shown in FIG. 7, the near-vertical line at the center of the graph is the zone plate focal length. It is to be understood that the tolerance for manufacturing can be quite high. The primarily effect of a small deviation from the designed radius of curvature is a shift in the DOW, it has a very small effect on other performances, such as bandwidth or throughput. In this example, a 10 $\mu$m or 0.17% error in the radius of curvature results in 0.003 nm or 0.023% shift in the operating wavelength.

When higher resolution than that discussed above is required for a large imaging field (e.g., lithographically printing 30 nm to 40 nm nodes), the EUV radiation's relative large wavelength requires a large numerical aperture (e.g., NA of approximately 0.25) lens, which demands very elaborate aberration corrections and severely reduces depth of field (0.2 $\mu$m). It is appreciated that shorter wavelength radiation is preferred because simpler aberration corrections may be adequate. For example, radiation of ~1 keV energy, which are used in proximity x-ray lithography, can be used in a lithography system using an AFO as the objective lens. In this case, the refractive lens 36 can be fabricated from copper (L-edge) or sodium based crystalline salt (sodium K-edge). FIG. 8 shows the focal length, $f_c$ of the AFO 30 (FIG. 4) with a 25 mm diameter, a 95 nm outer zone width, and a copper refractive element as a function of energy. If the refractive element has a radius of curvature of 500 mm, an achromatic bandwidth of 1 eV or 0.1% can be obtained. An equivalent Fresnel lens with a 0.5 $\mu$m thickness would have an outer zone width of 20 $\mu$m. The relatively narrow bandwidth results from the narrow L-absorption of copper. If alternatively a wider K-absorption edge of sodium is used, the bandwidth can be increased to three electron volts (3 eV), or three tenth of a percent (0.3%). It is recognized that if wider bandwidth is desired, an additional refractive lens can also be added to correct the chromatic aberration at three wavelengths, thus forming an apochromatic lens.

Current nano-fabrication technology can produce zone plates with an outer zone width small as approximately 20 nm. Therefore, AFOs of much higher resolution than the above examples can be produced. Example parameters are listed in Table 1. All the parameters listed in Table 1 are well within the limit of current fabrication technology and can be readily utilized to produce 20 nm structures in lithography applications.

It will be appreciated that if a concave refractive lens can be used in conjunction with the zone plate in the same scheme as described above to greatly enhance the chromaticity of the zone plate. The result is a focus element with high resolution in both spatial and energy domains. Also, note that the zone plate is not limited to a circular configuration as described. While the zone plate will focus in two dimensions if it is circular, a linear zone plate can be used if it is only necessary to focus in one dimension.

From the foregoing it will be appreciated that various lens configurations are possible. For example, by adding another downstream lens to expand bandwidth, it is possible to correct for three λ's. In other words, increasing the number of downstream refractive lenses (e.g., Fresnel lenses) will expand bandwidth. Similarly, additional diffractive lenses could be added upstream.

Figure 9:
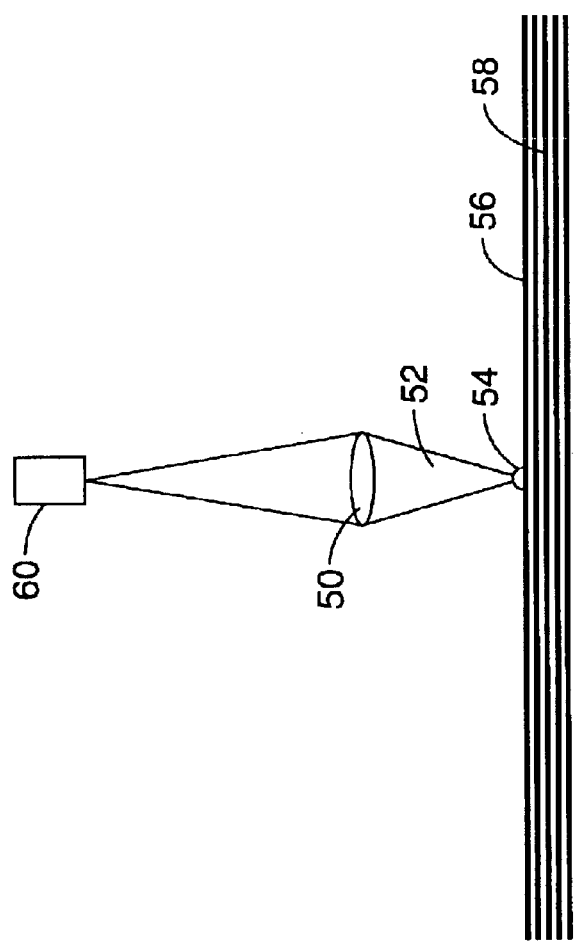
FIG. 9 is a schematic diagram of a basic AFO imaging/inspection system according to the present invention.

Based on the foregoing, it will be appreciated that the AFO of the present invention can be used for the development of reflective lithography mask inspection tools. By way of example, four AFO-based imaging system designs for achieving specific functions and applications will now be described. In all four embodiments, an AFO 50, e.g., the AFO described in detail above, is used to image light 52 from a defect particle 54 or a surface 56 of a multilayer mask blank 58 to a detector 60, as shown in FIG. 9.

In two of the imaging/inspection system designs, the AFO is used in a dark field imaging mode. In other words, the AFO does not intercept the beam illuminating the object, so that the image is created by photons that are scattered into the field of view by structures in the object.

The first two imaging systems differ in their detectors and applications. The first imaging system design uses a single element detector to record the scattered photons as a function of the position of the object when it is scanned in a raster fashion. Its main application is for inspecting mask blanks for extreme ultraviolet lithography applications. The second imaging system uses an array detector with suitable spatial resolution. It is located at the imaging plane of the AFO while the test object is located at the object plane. Its main applications include performing metrology measurement of patterned multilayer masks or imaging and classifying defects on a multilayer mask blank.

The third imaging system is essentially a microscope using the AFO as the objective operating in a bright field imaging mode. Its main applications include performing metrology measurement of a patterned multilayer masks or imaging and classifying defects on a multilayer mask blank. The fourth imaging system is a microscope using the AFO as the objective operating in a phase contrast imaging mode. Its main applications are similar to those of the dark field and the bright field imaging modes but may offer higher sensitivity with a somewhat more complex optical train.

Figure 10:
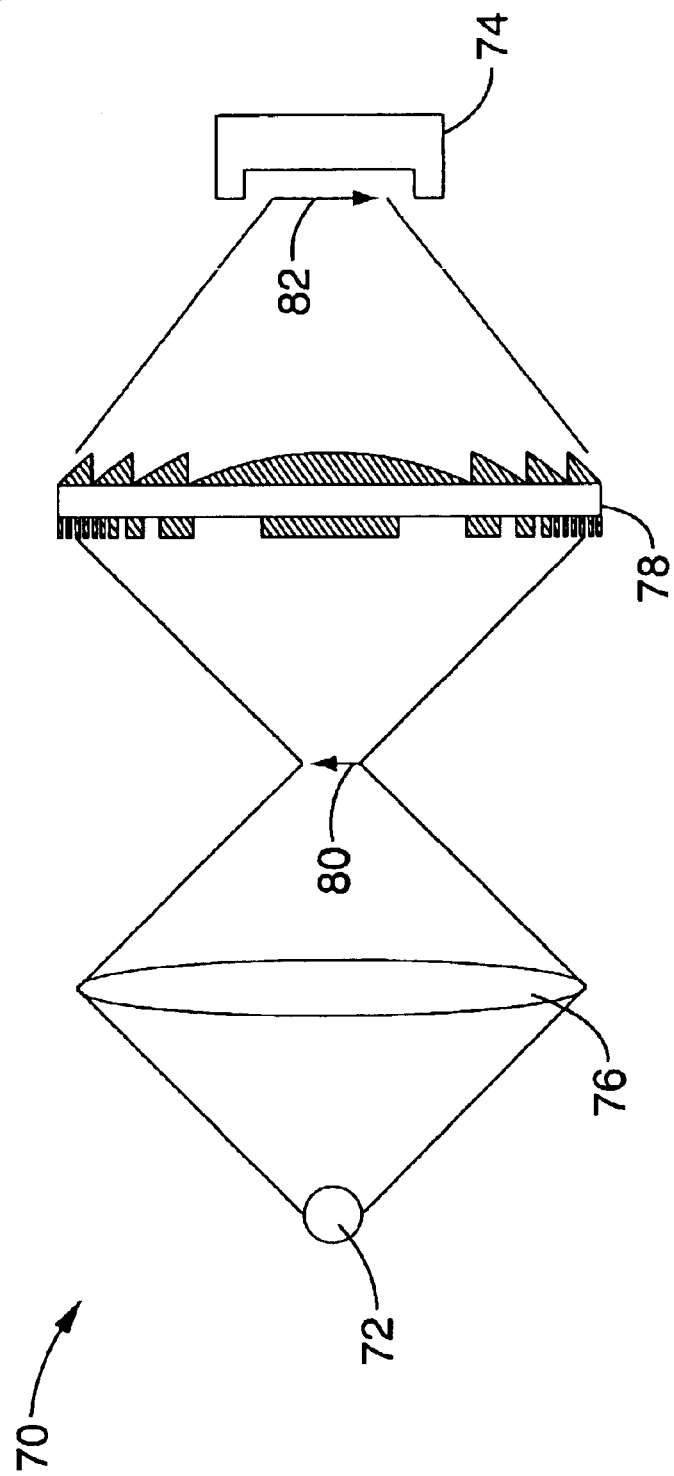
FIG. 10 is a schematic diagram of a bright-field imaging microscope according to the present invention.

Referring to FIG. 10, a bright-field imaging microscope is shown and is generally designated 70. FIG. 10 shows a radiation source 72 that is placed a predetermined distance from a detector 74. A condenser lens 76 and an AFO 78 are placed between the radiation source 72 and the detector 74. Specifically, as shown, the condenser lens 76 is placed closer to the radiation source 72 and the AFO 78 is placed closer to the detector 74. FIG. 10 further shows that an object 80 can be placed between the condenser lens 76 and the AFO 78. Preferably, the radiation generated by the radiation source 72 can be focused onto the object 80 by the condenser lens 76. The AFO 78 can produce an image 82 on the detector 74 from the radiation beam after the radiation beam passes the object 80. In this mode, only the absorption map of the object is imaged.

It is to be understood that in a preferred embodiment, the AFO 78 shown in FIG. 10 has a relatively high resolution, e.g., as small as twenty five nanometers (25 nm). Moreover, the AFO 78 has a relatively large imaging field, e.g., an imaging field of a few millimeters in diameter, and a relatively wide bandwidth, e.g., about one percent (1%) near the silicon L absorption edge at twelve and four-tenths nanometers (12.4 nm). In a non-limiting example, the AFO 78 can have an outer-most zone width of fifty nanometers (50 nm). This zone width corresponds to a numerical aperture of approximately twenty-five hundredths (0.25) for EUV radiation of thirteen and one half nanometers (13.5 nm) and acceptance angle of about fifteen degrees (15°). It is to be understood that the Rayleigh resolution for an AFO is approximately the outer most zone width multiplied by one and twenty-two hundredths (1.22). For the above exemplary AFO having an outer most zone width of fifty nanometers (50 nm), the Rayleigh resolution is approximately sixty nanometers (60 nm).

Figure 11:
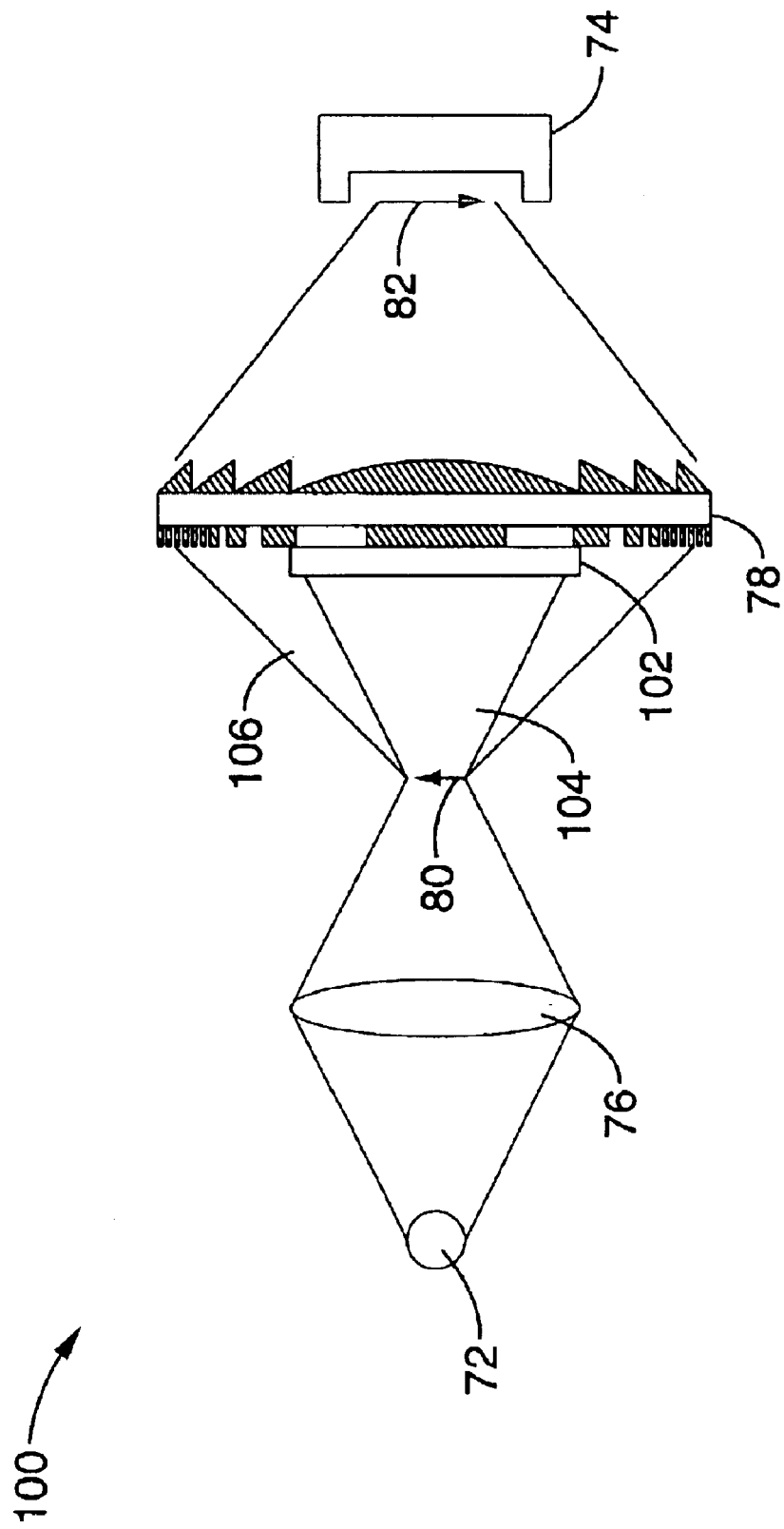
FIG. 11 is a schematic diagram of a dark-field imaging microscope according to the present invention.

Referring now to FIG. 11, a dark-field imaging microscope is shown and is generally designated 100. As shown, the dark-field imaging microscope 100 includes all of the same components as the bright-field imaging microscope, described above. In addition, the dark-field imaging microscope 100 includes a beam stop 102 placed adjacent to the AFO 78 on the object side of the AFO 78. In a preferred embodiment, the beam stop 102 blocks a direct beam 104 that, otherwise, would pass through the AFO 78. As shown, only a scattered beam 106 is imaged by the AFO 78 onto the detector 74.

In this case, the image 82 is related to the norm of the atomic scattering factors $f_1^2+f_2^2$, so that both absorption and phase components of the object will contribute to the image formation. Generally, the dark-field mode provided by the dark-field imaging microscope can be used to rapidly scan a multilayer mask blank in order to identify defects over an even background or to enhance small features in a mask pattern. On the other hand, the bright-field mode, provided by the bright-field imaging microscope 70 (FIG. 11) can be better suited for imaging a feature's absorption map.

Figure 13:
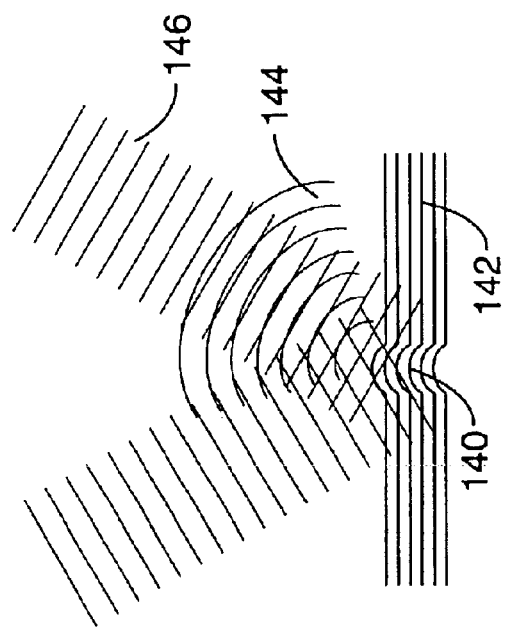
FIG. 13 is a schematic diagram illustrating light being reflected from a phase defect on a multilayer mask blank.
Figure 12:
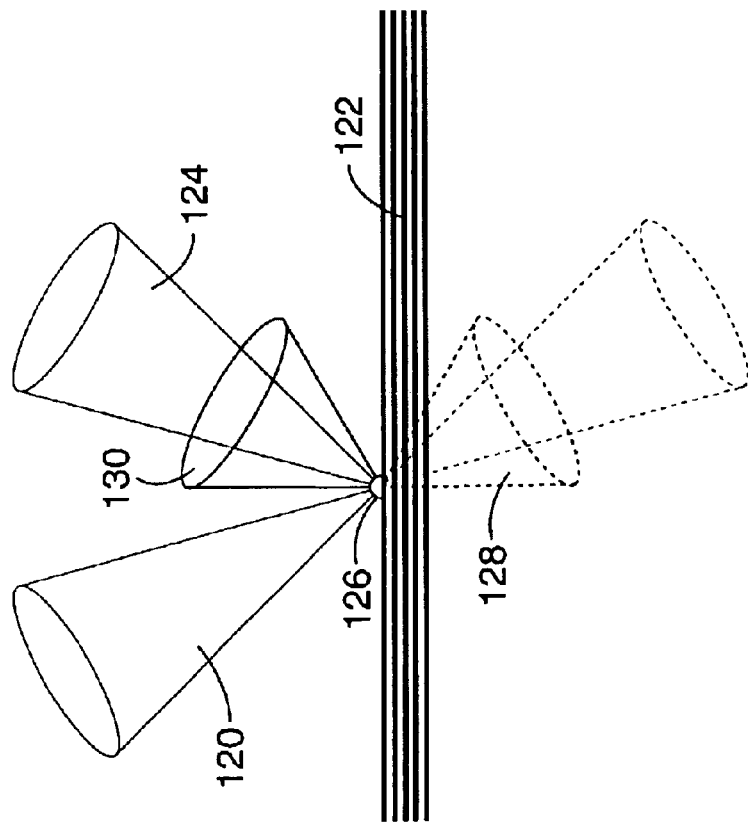
FIG. 12 is a schematic diagram illustrating light being scattering from a surface particle on a multilayer mask blank and light being reflected by the multilayer.

It is to be understood that potential defects include both amplitude and phase defects. An amplitude defect is a primarily absorptive feature on the surface of the mask, usually small particles. A phase defect is one that primarily causes a phase shift and little absorption, for an example, multilayers deposited over a particle on the substrate. Referring to FIG. 12, when focused EUV or x-ray radiation in an incident beam 120 impinges on the surface of a multilayer coated mask blank 122, a direct reflected beam 124 is reflected at the same incident angle—if the radiation wavelength matches the designed operating wavelength of the multilayer 122. If an amplitude defect particle 126 is present on the surface, part of the incident beam 120 can be scattered to establish a scattered beam 128. As shown, most of the scattered beam 128 is in the same direction as the incident beam 120. A portion of the scattered beam 128 can be reflected by the multilayer coating to establish a reflected scattered beam 130 in the same direction as the direct reflected beam 124. Similarly, as shown in FIG. 13, if a phase defect 140 is present in a multilayer 142, the wavefront of the reflection will be distorted and a broadened beam 144 will be added to a direct reflected beam 146.

Figure 14:
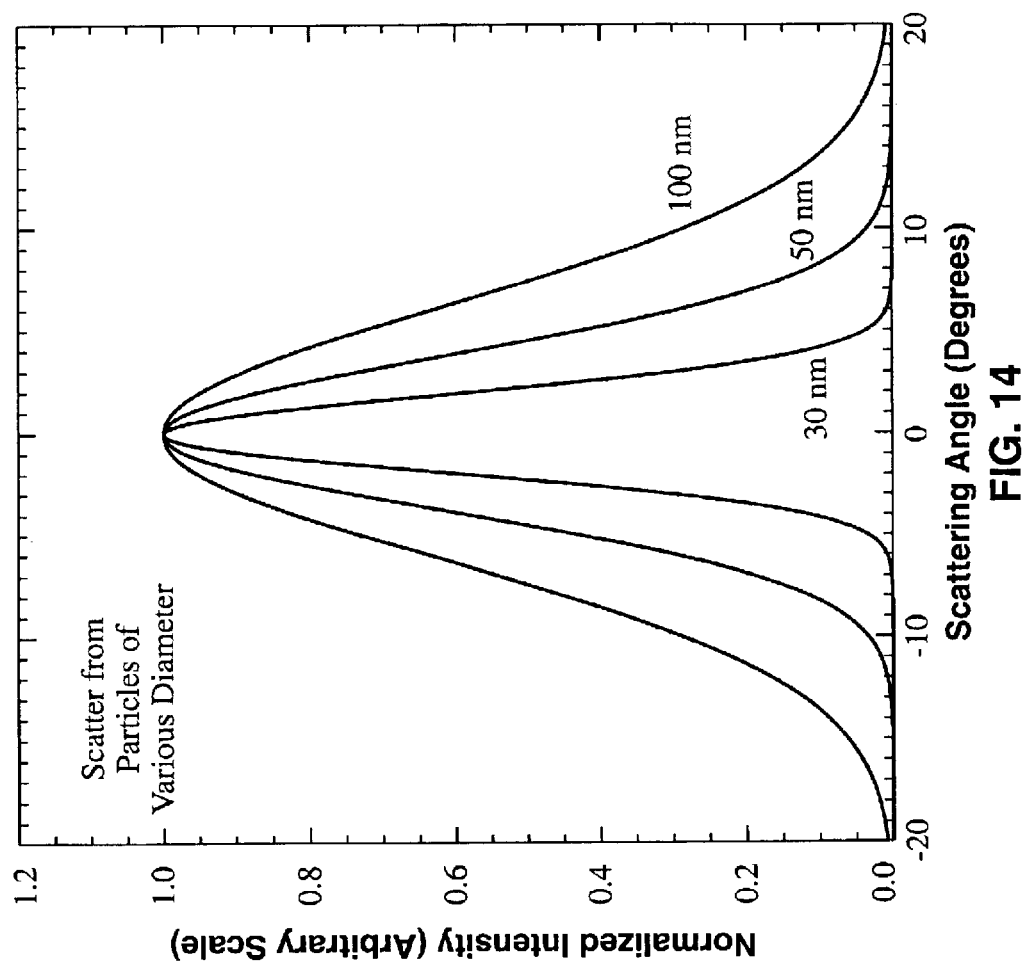
FIG. 14 is a graph of the angular distribution of scattered radiation from particles of various sizes.

In the case described in conjunction with FIG. 12, the direct reflected beam 124 and the reflected scattered beam 130 can be imaged for inspection purposes. Imaging only the direct reflected beam 124 results in the bright-field imaging mode, while imaging only the reflected scattered beam 130 results in the dark-field mode. The scattering intensity as a function of angle for small spherical particles is given by $$I = I_0\left(\frac{4\pi^3 r_0^2 R^6}{r^2}\right) n^2 (f_1^2 + f_2^2)(1 + \cos^2 2\theta)\left[\frac{J_{3/2}(u)}{u}\right] \quad (1)$$

where $r_0$ is the classical electron radius. R is the radius of the particle, r is the distance from the particle, n is the number of atoms per unit volume, and $j_{3/2}$ is the Bessel function of 3/2 order, and $u=4R\sin\theta/\lambda$. The central scattering peak for particles of 30, 50, and 100 nm diameters are plotted in FIG. 14. The range of scattering angle from 50 nm particles can be expected to be about 5° wider than the incident beam. If the reflected scattered beam 130 is to be imaged, the convergence angle of the incident beam 120 can be selected such that convergence angle of the resultant scattered beam approximately matches the acceptance angle of an AFO with a 50 nm outer most zone width. The total scattering cross-section is:

$$\sigma = \frac{8\pi^3 R^4}{\lambda^2}(\delta^2 + \beta^2) \quad (2)$$

For particles of 50 nm diameter, this is approximately 60 $nm^2$. (The maximum physical cross-section area is 1963 $nm^2$.) Note that the dependence on the feature size is to the fourth power. This property leads to a very high signal-to-noise ratio in the dark-field mode. The surface roughness of a mask blank is typically 0.15 nm RMS, which total cross-section on the order of $10^{-8}$ $nm^2$. For signal-to-noise of ratio of 100 to 1, a 400 μm by 400 μm area can be scanned each step. The intensity on the detector is essentially the product of the source brightness B, the condenser efficiency $\eta_C$, the sample scattering cross-section σ, multilayer reflectivity $\eta_M$, objective efficiency $\eta_Z$, detector efficiency $\eta_D$, and the acceptance solid angle Ω:

$$I = B\eta_C\sigma\eta_M\eta_Z\eta_D\Omega. \quad (3)$$

The expected values of the above parameters are:

| | |
|---|---|
| B | 1 W in-band or $10^{17}$ photons/(s $mm^2$ st. rad) |
| $\eta_C$ | 60% |
| σ | 60 $nm^2$ |
| $\eta_M$ | 60% |
| $\eta_Z$ | 20–50% |
| Ω | 0.2 |

These lead to an intensity of 1000 photons per second on the detector. Suppose 10 msec per step scanning times is used at 250 μm×250 μm step size, a signal ratio of over 400 can be expected with 100 count detected at the defect. A standard mask blank of 104 mm×132 mm blank requires less than 350000 steps, and less than 1 hour of inspection time.

Figure 15:
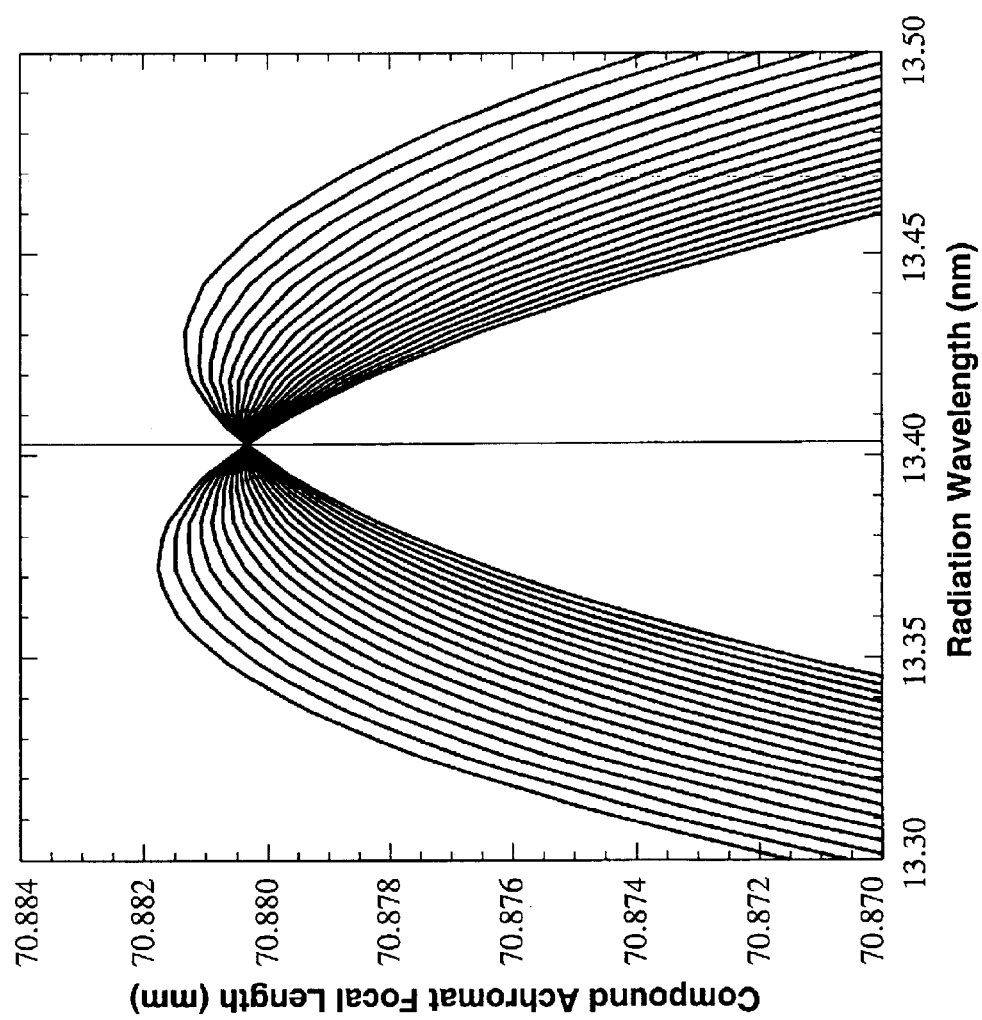
FIG. 15 is a graph of the working wavelength of an inventive AFO.
Figure 16:
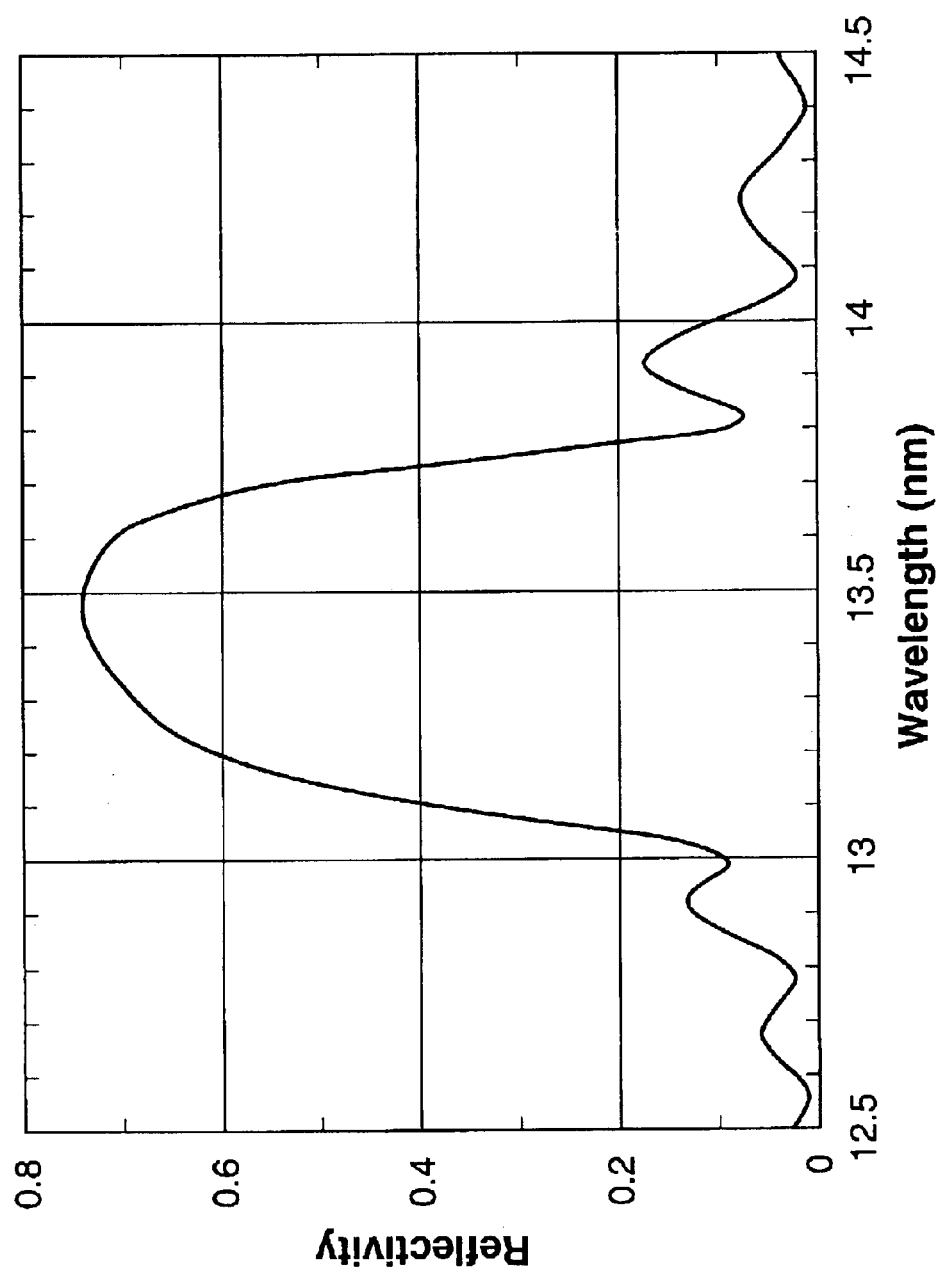
FIG. 16 is a graph of the reflectivity of a Si/Mo multilayer mask blank plotted versus wavelength.

The operating wavelength of the AFO (FIG. 15) can be matched to the operating wavelength of the mask's multilayer coating (FIG. 16), for example, about 13.4 nm for a Mo/Si multilayer coating at normal incidence. This configuration provides an ideal at or near operating wavelength, or actinic, inspection capability. The actinic imaging method is preferred because such inspection process most closely resembles the actual printing process. Hence the defects that will be printed is the same as that will be identified in the inspection tool. In particular, the bright-field imaging mode is the same as the actual printing process but with a different magnification. If the inspection tool operates at a different wavelength than the printing tool, the defects identified by the inspection tool will be different from what is actually printed.

Figure 17:
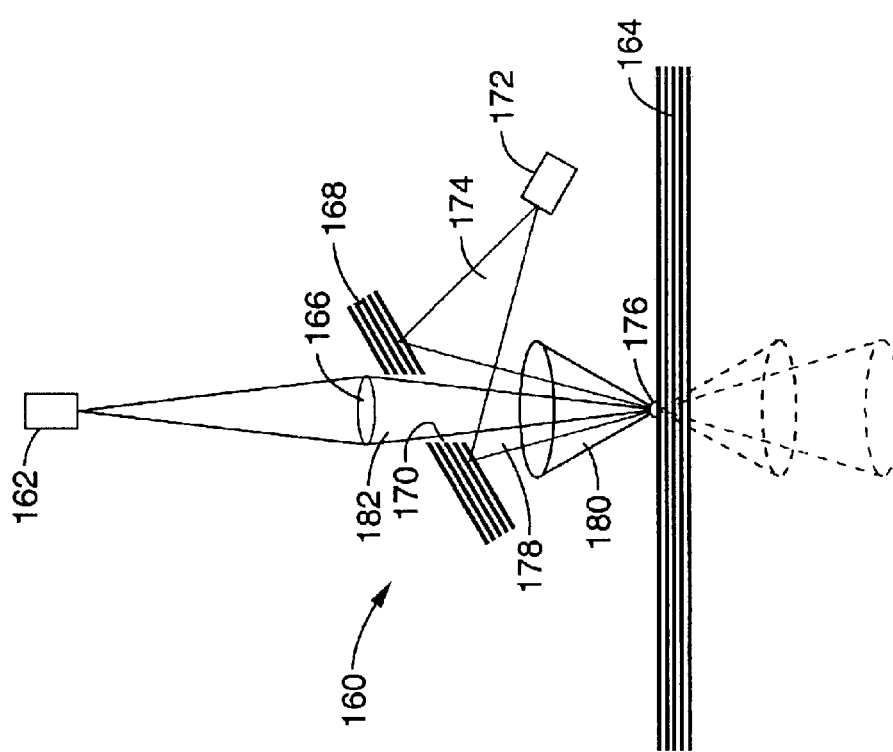
FIG. 17 is a schematic diagram of a normal-incidence inspection system according to the present invention.

Referring now to FIG. 17, a normal-incidence inspection system is shown and is generally designated 160. As shown, a detector 162 is placed a predetermined distance from a multilayer mask blank 164. An AFO 166, such as the AFO described in detail above, is placed between the detector 162 and the multilayer mask blank 164. Moreover, an apertured multilayer mirror 168 is placed between the AFO 166 and the multilayer mask blank 164. As shown, the multilayer mirror 168 is placed at a predetermined angle relative to the mask 164. Moreover, the apertured multilayer mirror 168 forms an aperture 170 through which radiation can pass in order to be focused by the AFO 166. FIG. 17 further shows a radiation source 172 that projects an incident beam 174 of radiation at the mask-facing side of the multilayer mirror 168. Also, a defect 176 is shown formed on the multilayer mask blank 164.

It is to be understood that the normal-incidence inspection system 160 can be used to inspect the multilayer mask blank 164 in the dark-field imaging mode. Moreover, the system 160 can rapidly scan the multilayer mask blank 164 to detect small defects, e.g., the defect 176, or image edges of the multilayer mask blank 164. EUV or x-ray radiation, i.e., the incident beam 174, provided by the radiation source 172 can be reflected to the multilayer mask blank 164 by the apertured multilayer mirror 168. It can be appreciated that the apertured multilayer mirror 168 can have a curved surface (not shown) that can be used to focus a reflected beam 178, or in the alternative, a condenser lens (not shown) can also be installed in the path of the reflected beam 178 to achieve focusing. The defect 176 present on the multilayer mask blank 164 can scatter the reflected beam 178 back toward the multilayer mirror 168 as a reflected scattered beam 180. As shown, the incident beam 174 and the reflected scattered beam 180 are reflected by the apertured multilayer mirror 168. Only a central part 182 of the reflected scattered beam 180 can pass through the mirror aperture 170 and be imaged to the detector 162 by the AFO 166.

Figure 18:
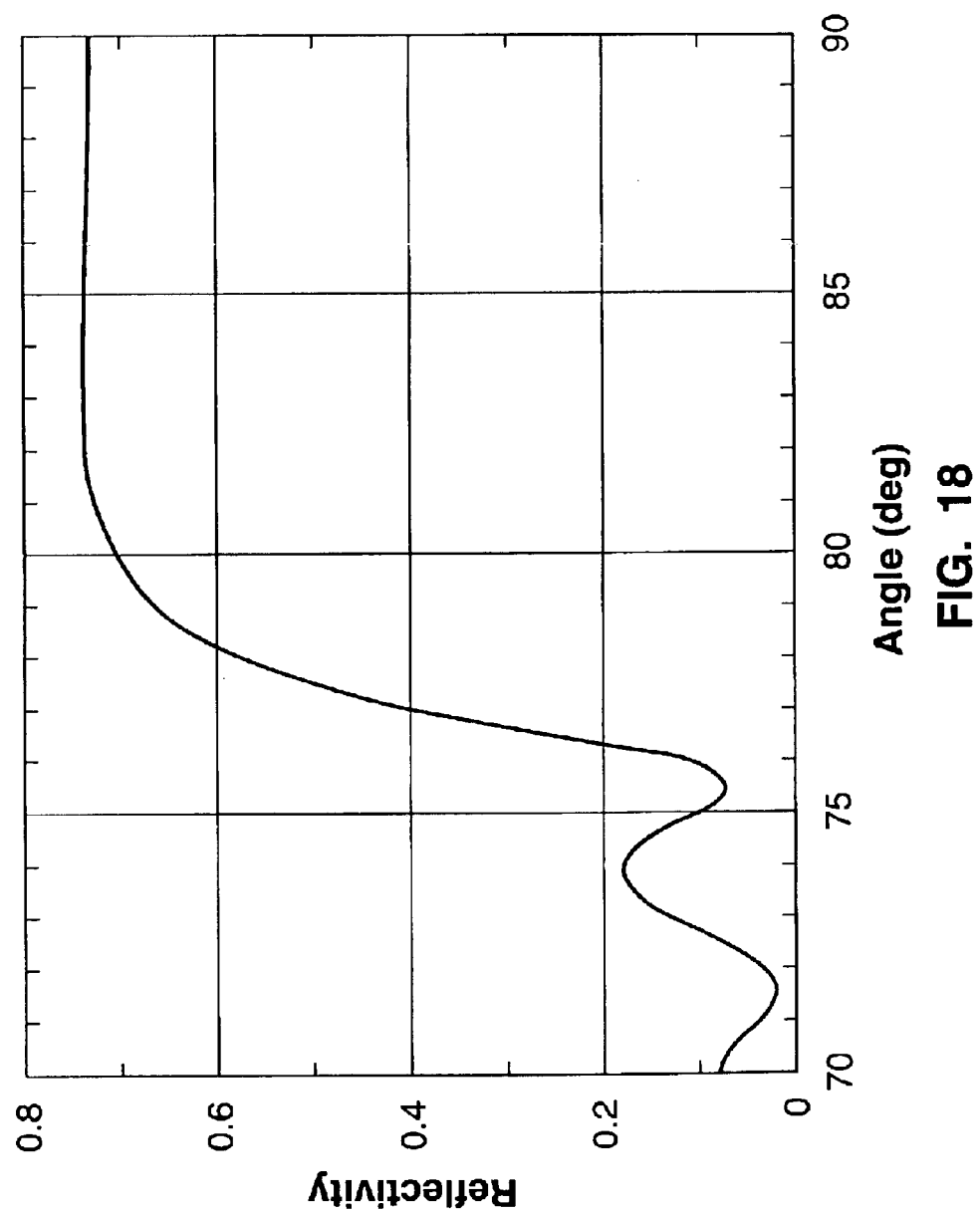
FIG. 18 is a graph of the reflectivity of a Si/Mo multilayer mask blank plotted versus incidence angle.

FIG. 18 shows that, in a preferred embodiment, the reflectivity of the apertured multilayer mirror 168 is very high and relatively constant up to about plus or minus fifteen degrees (±15°) incident angle, or a total of thirty degrees (30°), approximately twice the acceptance angle of the AFO lens with a fifty nanometer (50 nm) outer zone width. This system is well suited for detecting particles with a size of fifty nanometers (50 nm).

Figure 19:
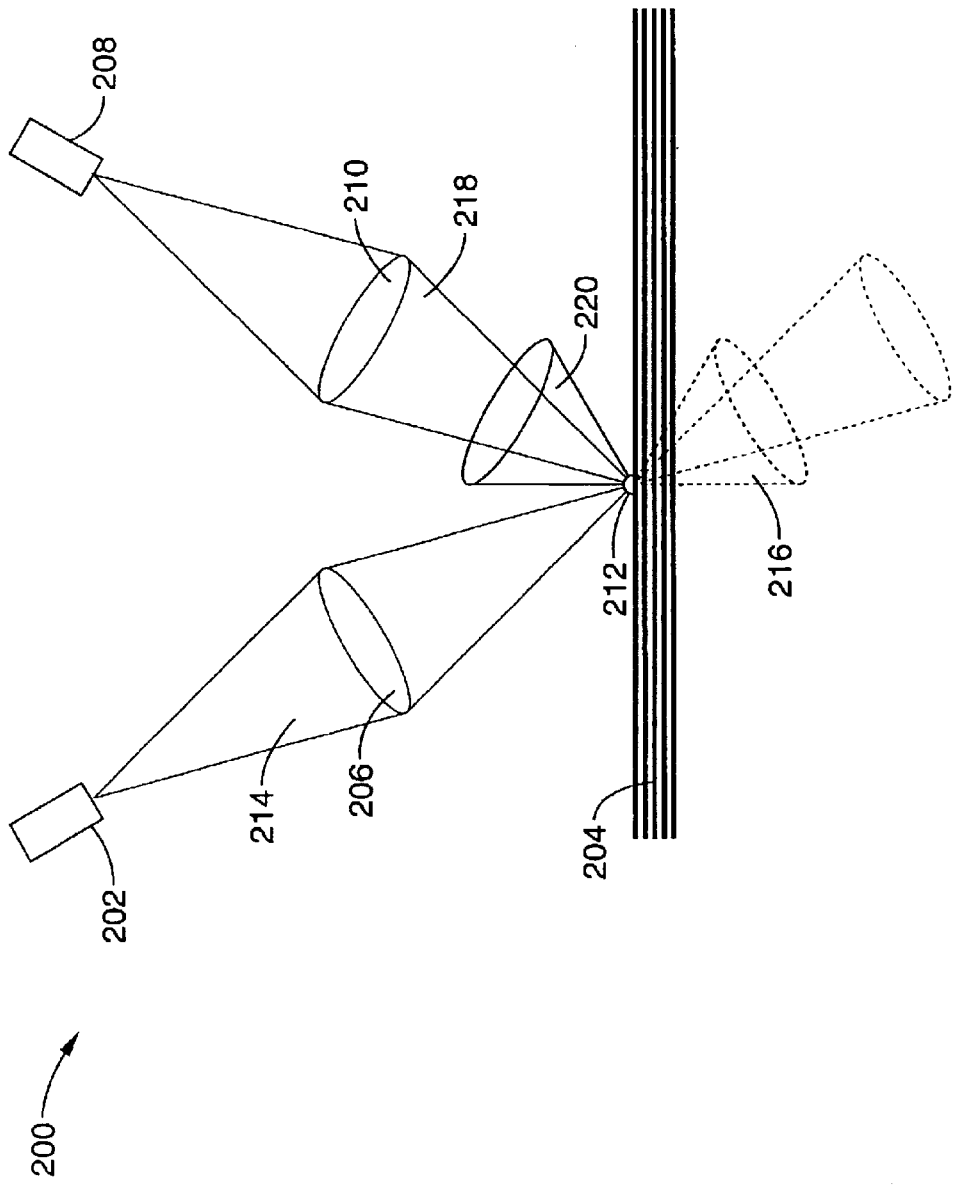
FIG. 19 is a schematic diagram of an oblique-incidence bright-field inspection system according to the present invention.

Referring now to FIG. 19, an oblique-incidence bright-field inspection system is shown and is generally designated 200. As shown, this system 200 includes a radiation source 202 that is distanced from a multilayer mask blank 204. It is to be understood that the radiation source 202 is placed at a predetermined angle with respect to the multilayer mask blank 204. Moreover, a condenser lens 206 is placed between the radiation source 202 and the multilayer mask blank 204.

FIG. 19 further shows a detector 208 that is placed at a predetermined angle and a predetermined distance from the multilayer mask blank 204. FIG. 19 shows that the distance of placement can be approximately the same as the distance at which the radiation source 202 is placed with respect to the multilayer mask blank 204. Also, as shown, the angle of placement of the detector 208 can be the same as, but opposite to, the angle of placement of the radiation source 202 with respect to the multilayer mask blank 204. In a preferred embodiment, an AFO 210, e.g. the AFO described in detail above, is placed between the detector 208 and the multilayer mask blank 204. FIG. 19 further shows a defect 212 established by the multilayer mask blank 204.

Figure 20:
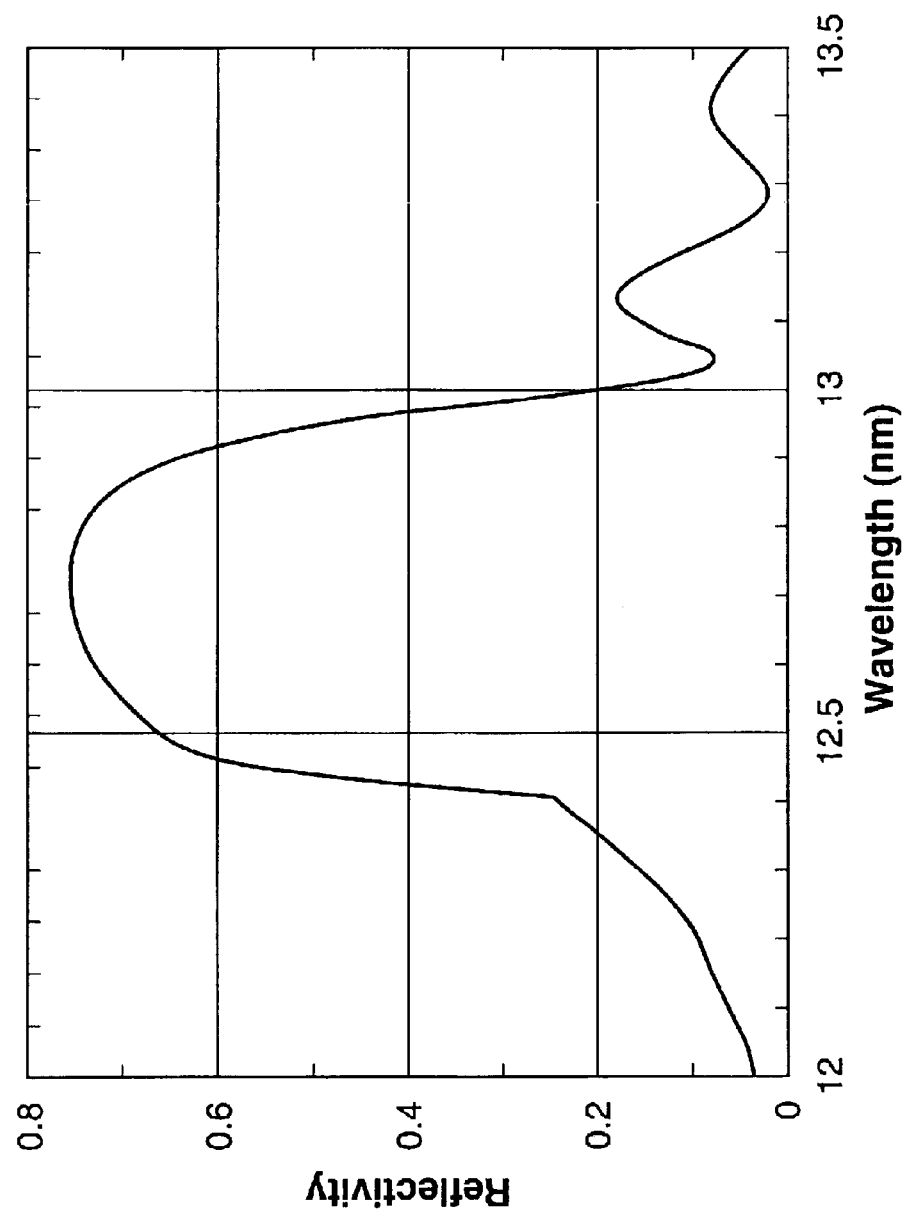
FIG. 20 is a graph of the reflectivity of a Si/Mo multilayer mask blank plotted versus wavelength for a seventy degree (70°) incidence angle.

It is to be understood that this system can used to inspect the multilayer mask blank 204 or pattern in the bright-field mode. In this system 200, the radiation source 202 emits an EUV or x-ray radiation incident beam 214, which can be focused to the multilayer mask blank 204 by the condenser 206. If a defect, e.g., the defect 212, is present on the multilayer mask blank 204, the incident beam 214 can be scattered by the defect 212 to establish a scattered beam 216. The multilayer mask blank 204 can reflect the incident beam 214 to establish a direct reflected beam 218 and the scattered beam 216 can be reflected to form a reflected scattered beam 220. The direct reflected beam 218 is imaged by the AFO lens 210 to the detector 208, while most of the reflected scattered beam 220 can be rejected. In this configuration, the radiation incident beam 214 should have a shorter wavelength than the designed operating wavelength of the multilayer mask blank. For example shown, as shown in FIG. 20, if the multilayer coating is designed to reflect thirteen and four-tenths nanometer (13.4 nm) radiation, and the incidence angle of the incident beam 214 is twenty degrees (20°), a wavelength of twelve and seven-tenths nanometers (12.7 nm) is appropriate.

Figure 21:
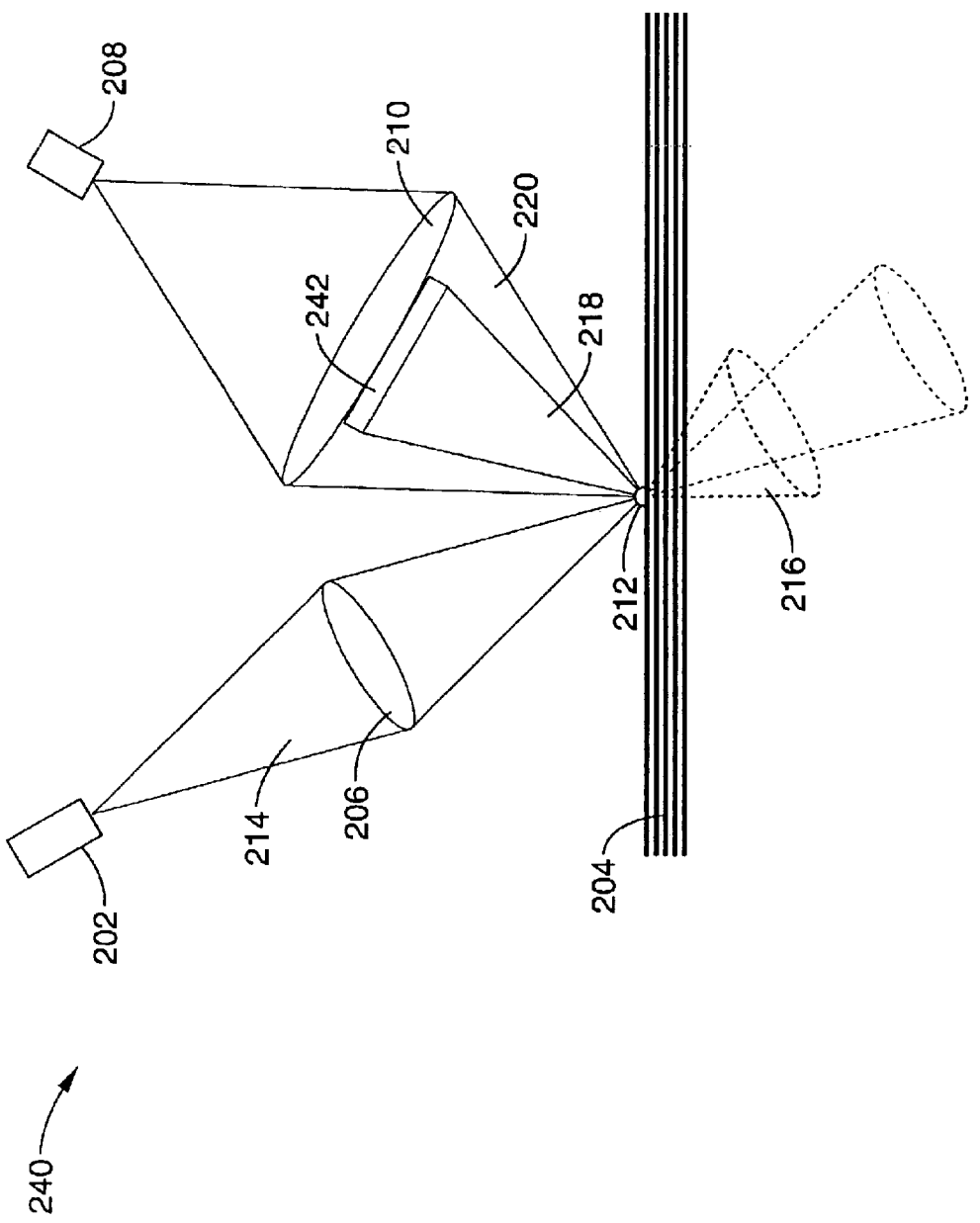
FIG. 21 is a schematic diagram of an oblique-incidence dark-field inspection system according to the present invention.

FIG. 21 shows an oblique-incidence dark-field inspection system that is generally designated 240. As shown, the oblique-incident dark-field inspection system 240 is identical to the oblique-incident bright-field inspection system shown in FIG. 19. In addition to all of the elements shown in FIG. 19, the system 240 shown in FIG. 21 includes a beam stop 242 that, preferably, is placed between the AFO 210 and the multilayer mask blank 204 immediately adjacent to the AFO 210.

In the dark-field mode provided, by the oblique-incident dark-field inspection system 240, the direct reflected beam 218 can be blocked by the beam stop 242. Moreover, the reflected scattered beam 220 can be imaged by the AFO lens 210 to the detector 208.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiments that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A normal-incidence inspection system for inspecting a mask blank, comprising:

at least one detector configured for being placed a predetermined distance from the mask blank;

at least one achromatic Fresnel objective (AFO) lens configured for being placed between the detector and the mask blank;

at least one mirror configured for being placed between the AFO lens and the mask blank;

at least one aperture established by the mirror, the aperture allowing radiation to pass through the mirror to the AFO lens; and at least one radiation source configured for providing an incident beam of radiation that is reflected by the mirror to the mask blank;

wherein said AFO lens comprises a diffractive lens and a refractive lens formed on opposite sides of a common substrate.

2. A system as in claim 1, wherein the detector comprises a single detector.

3. A system as in claim 1, wherein the detector comprises an array of detectors.

4. A system as in claim 1, wherein the mirror is configured to reflect the incident beam as a reflected beam that is normal to a surface of the mask blank.

5. A system as in claim 4, wherein when a defect is encountered, the defect scatters the reflected beam back toward the mirror as a reflected scattered beam and the mirror blocks a portion of the reflected scattered beam from reaching the AFO lens.

6. A system as in claim 5, wherein a central portion of the reflected scattered beam passes through the aperture formed by the mirror.

7. A system as in claim 6, wherein the central portion of the reflected scattered beam is imaged to the detector by the AFO lens.

8. A system as in claim 1, wherein the mask blank is a multilayer mask blank.

9. A system as in claim 8, wherein the multilayer mask blank is a patterned multilayer mask blank.

10. A system as in claim 1, wherein the mirror comprises a multilayer mirror.

11. A system as in claim 1, wherein the diffractive lens comprises a Fresnel zone plate.

12. A system as in claim 11, wherein the refractive lens comprises a refractive Fresnel lens.

13. A system as in claim 1, wherein the radiation source provides extreme ultraviolet radiation.

14. A system as in claim 1, wherein the radiation source provides x-ray radiation.

15. A method for imaging an object, comprising:

directing a beam of radiation at an object; and producing an image of the object at a detector using an achromatic Fresnel objective comprising a diffractive lens and a refractive lens formed on opposite sides of a common substrate.

16. A method as in claim 15, further comprising:

blocking a portion of the beam of radiation using a beam stop.

17. A method as in claim 16, wherein the radiation comprises x-ray radiation.

18. A method as in claim 16, wherein the radiation comprises extreme ultraviolet radiation.

19. A method as in claim 15, wherein the diffractive lens comprises a Fresnel zone plate.

20. A method as in claim 19, wherein the refractive lens comprises a refractive Fresnel lens.

21. A method for inspecting a mask blank, comprising:

directing an incident beam of radiation at a mask blank; and producing an image at a detector using an achromatic Fresnel objective, the image being produced at least partially from a reflected beam of radiation;

said achromatic Fresnel objective comprising a diffractive lens and a refractive lens formed a opposite sides of a common substrate.

22. A method as in claim 21, wherein when a defect in the mask blank is encountered, a reflected scattered beam of radiation is created and the image is produced at least partially from the reflected scattered beam of radiation.

23. A method as in claim 21, further comprising:

reflecting the incident beam off of a mirror in order to establish a reflected beam that is normal to the mask blank.

24. A method as in claim 21, wherein the incident beam is angled with respect to the mask blank.

25. A method as in claim 21, further comprising:

blocking a portion of the reflected beam of radiation from passing through the AFO using a beam stop.

26. A method as in claim 21, wherein the radiation comprises x-ray radiation.

27. A method as in claim 21, wherein the radiation comprises extreme ultraviolet radiation.

28. A method as in claim 21, wherein the AFO comprises:

at least one diffractive tens; and at least one refractive lens.

29. A method as in claim 28, wherein the diffractive lens and the refractive lens are formed on a common substrate.

30. A method as in claim 29, wherein the diffractive lens comprises a Fresnel zone plate.

31. A method as in claim 30, wherein the refractive lens comprises a refractive Fresnel lens.

* * * * *